US012673199B2

(12) United States Patent
Kaib et al.

(10) Patent No.: US 12,673,199 B2
(45) Date of Patent: *Jul. 7, 2026

(54) WEARABLE THERAPEUTIC DEVICE

(71) Applicant: ZOLL Medical Corporation,
Chelmsford, MA (US)

(72) Inventors: Thomas E Kaib, Irwin, PA (US);
Shane S Volpe, Saltsburg, PA (US);
Emil Oskin, Natrona Heights, PA (US)

(73) Assignee: ZOLL Medical Corporation,
Chelmsford, MA (US)

( * ) Notice: Subject to any disclaimer, the term of this
patent is extended or adjusted under 35
U.S.C. 154(b) by 0 days.

This patent is subject to a terminal dis-
claimer.

(21) Appl. No.: 18/621,984

(22) Filed: Mar. 29, 2024

(65) Prior Publication Data

US 2024/0238585 A1     Jul. 18, 2024

Related U.S. Application Data

(60) Division of application No. 17/480,480, filed on Sep.
21, 2021, now Pat. No. 11,975,186, which is a
(Continued)

(51) Int. Cl.
*A61N 1/04*         (2006.01)
*A61N 1/39*         (2006.01)
(52) U.S. Cl.
CPC ........... *A61N 1/0484* (2013.01); *A61N 1/046*
(2013.01); *A61N 1/3906* (2013.01);
(Continued)
(58) Field of Classification Search
CPC ............................. A61N 1/0484; A61N 1/3904
See application file for complete search history.

(56) References Cited

U.S. PATENT DOCUMENTS 4,094,310  A     6/1978  McEachern et al.
4,632,122  A    12/1986  Johansson et al.
(Continued)

FOREIGN PATENT DOCUMENTS

DE     2644236     4/1981
EP     0335356    10/1989
(Continued)

OTHER PUBLICATIONS

American Journal of Respiratory and Critical Care Medicine, vol.
166, pp. 111-117 (2002). American Thoracic Society, ATS State-
ment: Guidelines for the Six-Minute Walk Test, available at http://
www.atsjournals.org/doi/full/10.1164/ajrccm.166.1.at1102.
(Continued)

*Primary Examiner* — Allen Porter
(74) *Attorney, Agent, or Firm* — ZOLL Medical
Corporation

(57) ABSTRACT

A wearable monitoring and therapeutic device includes at
least two sensing electrodes. Each sensing electrode
includes a metallic surface integrated in a garment. The
device includes at least two therapy electrodes. Each of the
at least two therapy electrodes includes a receptacle, and
each receptacle includes at least one dose of conductive
fluid. The device includes the garment. The garment
includes a fabric that is stretchable and that is breathable
and/or moisture wicking, and conductive wiring configured
to at least partially electrically connect that at least two
sensing electrodes to at least one defibrillator component.
The device includes the at least one defibrillator component.
The at least two therapy electrodes are configured to provide
an electric shock to the subject. Prior to the application of the
electric shock, each receptacle is configured to release the
conductive fluid from the receptacle.

15 Claims, 19 Drawing Sheets

Related U.S. Application Data continuation of application No. 17/197,645, filed on Mar. 10, 2021, now Pat. No. 11,872,390, which is a continuation of application No. 16/747,876, filed on Jan. 21, 2020, now Pat. No. 11,278,714, which is a continuation of application No. 16/202,325, filed on Nov. 28, 2018, now Pat. No. 10,589,083, which is a continuation of application No. 15/644,069, filed on Jul. 7, 2017, now Pat. No. 10,183,160, which is a continuation of application No. 14/875,132, filed on Oct. 5, 2015, now Pat. No. 9,956,392, which is a continuation of application No. 14/625,886, filed on Feb. 19, 2015, now Pat. No. 9,457,178, which is a continuation of application No. 13/109,079, filed on May 17, 2011, now Pat. No. 9,008,801.

(60) Provisional application No. 61/426,347, filed on Dec. 22, 2010, provisional application No. 61/345,947, filed on May 18, 2010.

(52) U.S. Cl.
CPC ......... *A61N 1/3918* (2013.01); *A61N 1/3925* (2013.01); *A61N 1/3987* (2013.01); *A61N 1/3993* (2013.01); *A61N 1/3968* (2013.01)

(56) References Cited

U.S. PATENT DOCUMENTS

| | | | |
|---|---|---|---|
| 4,928,690 A | | 5/1990 | Heilman et al. |
| 4,978,926 A | | 12/1990 | Zerod et al. |
| 5,062,834 A | | 11/1991 | Gross et al. |
| 5,078,134 A | | 1/1992 | Heilman et al. |
| 5,348,008 A | | 9/1994 | Bornn et al. |
| 5,357,696 A | | 10/1994 | Gray et al. |
| 5,365,932 A | | 11/1994 | Greenhut |
| 5,472,453 A | | 12/1995 | Alt |
| 5,662,689 A | | 9/1997 | Elsberry et al. |
| 5,718,242 A | | 2/1998 | McClure et al. |
| 5,738,102 A | | 4/1998 | Lemelson |
| 5,741,306 A | | 4/1998 | Glegyak et al. |
| 5,758,443 A | | 6/1998 | Pedrazzini |
| 5,792,190 A | | 8/1998 | Olson et al. |
| 5,871,534 A | * | 2/1999 | Messick ............... A61N 1/0456 600/382 |
| 5,929,601 A | | 7/1999 | Kaib et al. |
| 5,944,669 A | | 8/1999 | Kaib |
| 6,016,445 A | | 1/2000 | Baura |
| 6,065,154 A | | 5/2000 | Hulings et al. |
| 6,097,982 A | | 8/2000 | Glegyak et al. |
| 6,097,987 A | | 8/2000 | Milani |
| 6,148,233 A | | 11/2000 | Owen et al. |
| 6,169,387 B1 | | 1/2001 | Kaib |
| 6,169,397 B1 | | 1/2001 | Steinbach et al. |
| 6,253,099 B1 | | 6/2001 | Oskin et al. |
| 6,280,461 B1 | | 8/2001 | Glegyak et al. |
| 6,390,996 B1 | | 5/2002 | Halperin et al. |
| 6,532,379 B2 | | 3/2003 | Stratbucker |
| 6,681,003 B2 | | 1/2004 | Linder et al. |
| 6,690,969 B2 | | 2/2004 | Bystrom et al. |
| 6,804,554 B2 | | 10/2004 | Ujhelyi et al. |
| 6,827,695 B2 | | 12/2004 | Palazzolo et al. |
| 6,865,413 B2 | | 3/2005 | Halperin et al. |
| 6,908,437 B2 | | 6/2005 | Bardy |
| 6,944,498 B2 | | 9/2005 | Owen et al. |
| 6,990,373 B2 | | 1/2006 | Jayne et al. |
| 7,074,199 B2 | | 7/2006 | Halperin et al. |
| 7,108,665 B2 | | 9/2006 | Halperin et al. |
| 7,118,542 B2 | | 10/2006 | Palazzolo et al. |
| 7,122,014 B2 | | 10/2006 | Palazzolo et al. |
| 7,149,579 B1 | | 12/2006 | Koh et al. |
| 7,220,235 B2 | | 5/2007 | Geheb et al. |
| 7,295,871 B2 | | 11/2007 | Halperin et al. |
| 7,340,296 B2 | | 3/2008 | Stahmann et al. |
| 7,453,354 B2 | | 11/2008 | Reiter et al. |
| 7,476,206 B2 | | 1/2009 | Palazzolo et al. |
| 7,488,293 B2 | | 2/2009 | Marcovecchio et al. |
| 7,522,951 B2 | | 4/2009 | Gough et al. |
| 7,831,303 B2 | | 11/2010 | Rueter et al. |
| 7,904,153 B2 | | 3/2011 | Greenhut et al. |
| 7,974,689 B2 | | 7/2011 | Volpe et al. |
| 8,121,683 B2 | | 2/2012 | Bucher et al. |
| 8,140,154 B2 | | 3/2012 | Donnelly et al. |
| 8,271,082 B2 | | 9/2012 | Donnelly et al. |
| 9,427,564 B2 | | 8/2016 | Kaib et al. |
| 9,492,105 B1 | * | 11/2016 | Kayyali ............... A61B 5/0535 |
| 9,937,355 B2 | | 4/2018 | Kaib et al. |
| 2003/0004547 A1 | | 1/2003 | Owen et al. |
| 2003/0055460 A1 | | 3/2003 | Owen et al. |
| 2003/0095648 A1 | | 5/2003 | Kaib et al. |
| 2003/0149462 A1 | | 8/2003 | White et al. |
| 2003/0158593 A1 | | 8/2003 | Heilman et al. |
| 2003/0174049 A1 | | 9/2003 | Beigel et al. |
| 2003/0195567 A1 | | 10/2003 | Jayne et al. |
| 2003/0212311 A1 | | 11/2003 | Nova et al. |
| 2004/0007970 A1 | | 1/2004 | Ma et al. |
| 2004/0162510 A1 | | 8/2004 | Jayne et al. |
| 2004/0249419 A1 | | 12/2004 | Chapman et al. |
| 2005/0049515 A1 | | 3/2005 | Misczynski et al. |
| 2005/0131465 A1 | | 6/2005 | Freeman et al. |
| 2006/0036292 A1 | | 2/2006 | Smith et al. |
| 2006/0085049 A1 | | 4/2006 | Cory et al. |
| 2006/0211934 A1 | | 9/2006 | Hassonjee et al. |
| 2006/0220809 A1 | | 10/2006 | Stigall et al. |
| 2006/0264776 A1 | | 11/2006 | Stahmann et al. |
| 2006/0270952 A1 | | 11/2006 | Freeman et al. |
| 2007/0028821 A1 | | 2/2007 | Bennett et al. |
| 2007/0060993 A1 | | 3/2007 | Craige, III et al. |
| 2007/0073120 A1 | | 3/2007 | Li et al. |
| 2007/0118056 A1 | | 5/2007 | Wang et al. |
| 2007/0161913 A1 | | 7/2007 | Farrell et al. |
| 2007/0169364 A1 | | 7/2007 | Townsend et al. |
| 2007/0239220 A1 | | 10/2007 | Greenhut et al. |
| 2007/0265671 A1 | | 11/2007 | Roberts et al. |
| 2008/0004536 A1 | | 1/2008 | Baxi et al. |
| 2008/0021532 A1 | | 1/2008 | Kveen et al. |
| 2008/0030656 A1 | | 2/2008 | Watson et al. |
| 2008/0031270 A1 | | 2/2008 | Tran et al. |
| 2008/0033495 A1 | | 2/2008 | Kumar |
| 2008/0045815 A1 | | 2/2008 | Derchak et al. |
| 2008/0046015 A1 | | 2/2008 | Freeman et al. |
| 2008/0058884 A1 | | 3/2008 | Matos |
| 2008/0249591 A1 | | 10/2008 | Gaw et al. |
| 2008/0306560 A1 | | 12/2008 | Macho et al. |
| 2008/0306562 A1 | | 12/2008 | Donnelly et al. |
| 2008/0306566 A1 | | 12/2008 | Holmstrom et al. |
| 2008/0312709 A1 | | 12/2008 | Volpe et al. |
| 2009/0073991 A1 | | 3/2009 | Landrum et al. |
| 2009/0076336 A1 | | 3/2009 | Mazar et al. |
| 2009/0076340 A1 | | 3/2009 | Libbus et al. |
| 2009/0076341 A1 | | 3/2009 | James et al. |
| 2009/0076342 A1 | | 3/2009 | Amurthur et al. |
| 2009/0076343 A1 | | 3/2009 | James et al. |
| 2009/0076344 A1 | | 3/2009 | Libbus et al. |
| 2009/0076345 A1 | | 3/2009 | Manicka et al. |
| 2009/0076346 A1 | | 3/2009 | James et al. |
| 2009/0076348 A1 | | 3/2009 | Manicka et al. |
| 2009/0076349 A1 | | 3/2009 | Libbus et al. |
| 2009/0076350 A1 | | 3/2009 | Bly et al. |
| 2009/0076363 A1 | | 3/2009 | Bly et al. |
| 2009/0076364 A1 | | 3/2009 | Libbus et al. |
| 2009/0076397 A1 | | 3/2009 | Libbus et al. |
| 2009/0076405 A1 | | 3/2009 | Amurthur et al. |
| 2009/0076410 A1 | | 3/2009 | Libbus et al. |
| 2009/0076559 A1 | | 3/2009 | Libbus et al. |
| 2009/0088652 A1 | | 4/2009 | Tremblay |
| 2009/0093687 A1 | | 4/2009 | Telfort et al. |
| 2009/0138059 A1 | | 5/2009 | Ouwerkerk |
| 2009/0234410 A1 | | 9/2009 | Libbus et al. |
| 2009/0264792 A1 | | 10/2009 | Mazar |
| 2009/0275848 A1 | | 11/2009 | Brockway et al. |
| 2009/0287120 A1 | | 11/2009 | Ferren et al. |

(56)　　　　　References Cited

U.S. PATENT DOCUMENTS

| | | | |
|---|---|---|---|
| 2009/0292194 A1 | 11/2009 | Libbus et al. |
| 2009/0326595 A1 | 12/2009 | Brockway et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0234716 A1 | 9/2010 | Engel |
| 2010/0298899 A1 | 11/2010 | Donnelly et al. |
| 2011/0077728 A1 | 3/2011 | Li et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0146797 A1 | 6/2012 | Oskin et al. |
| 2012/0150008 A1 | 6/2012 | Kaib et al. |

FOREIGN PATENT DOCUMENTS

| | | |
|---|---|---|
| EP | 0459239 | 12/1991 |
| EP | 0295497 | 9/1993 |
| EP | 1455640 | 1/2008 |
| EP | 2083104 | 7/2009 |
| EP | 1720446 | 7/2010 |
| JP | 5115450 | 5/1993 |
| JP | 2006512128 | 4/2006 |
| JP | 2006223168 | 8/2006 |
| JP | 2009510276 | 3/2009 |
| WO | 2000002484 | 1/2000 |
| WO | 2004054656 | 7/2004 |
| WO | 2006050235 | 5/2006 |
| WO | 2007057169 | 5/2007 |
| WO | 2007077997 | 7/2007 |
| WO | 2015056262 | 4/2015 |

OTHER PUBLICATIONS

De Bock et al., "Captopril treatment of chronic heart failure in the very old," J. Gerontol. (1994) 49: M148-M152.

http://www.web.archive.org/web/20030427001846/http:/www.lifecor.com/imagelib/imageproduct.asp.Published by LifeCor, Inc., 2002, on a webpage owned by LifeCor, Inc.

O'Keeffe et al., "Reproducibility and responsiveness of quality of the assessment and six minute walk test in elderly heart failure patients," Heart (1998) 80: 377-382.

* cited by examiner

Metal
Foil
*1605*

Conductive
Stitching
*135, 140, 150, 505*

Elastic
Material

Garment
Worn By
Patient
*105*

Conductive
Stitching
*505*

Connection
Snap
*1505*

Electrode
Perforated
*135, 140, 150*

Air Flow/
Body Heat

Breathable
Fabric
*105*

Subject's Skin

WEARABLE THERAPEUTIC DEVICE

CROSS REFERENCE TO RELATED APPLICATIONS

This application claims priority under 35 U.S.C. § 120 as a divisional of U.S. patent application Ser. No. 17/480,480, titled "Wearable Therapeutic Device," filed Sep. 21, 2021, which claims priority under 35 U.S.C. § 120 as a continuation of U.S. patent application Ser. No. 17/197,645, titled "Wearable Therapeutic Device," filed Mar. 10, 2021, now U.S. Pat. No. 11,872,390, which claims priority under 35 U.S.C. § 120 as a continuation of U.S. patent application Ser. No. 16/747,876, titled "Wearable Therapeutic Device," filed Jan. 21, 2020, now U.S. Pat. No. 11,278,714, which claims priority under 35 U.S.C. § 120 as a continuation of U.S. patent application Ser. No. 16/202,325, titled "Wearable Therapeutic Device," filed Nov. 28, 2018, now U.S. Pat. No. 10,589,083, which claims priority under 35 U.S.C. § 120 as a continuation of U.S. patent application Ser. No. 15/644,069, titled "Wearable Therapeutic Device," filed Jul. 7, 2017, now U.S. Pat. No. 10,183,160, which claims priority under 35 U.S.C. § 120 as a continuation of U.S. patent application Ser. No. 14/875,132, titled "Wearable Therapeutic Device," filed Oct. 5, 2015, now U.S. Pat. No. 9,956,392, which claims priority under 35 U.S.C. § 120 as a continuation of U.S. patent application Ser. No. 14/625,886, titled "Wearable Therapeutic Device System," filed Feb. 19, 2015, now U.S. Pat. No. 9,457,178, which claims priority under 35 U.S.C. § 120 as a continuation of U.S. patent application Ser. No. 13/109,079, titled "Wearable Therapeutic Device," filed May 17, 2011, now U.S. Pat. No. 9,008,801, which claims priority under 35 U.S.C. § 119(c) to U.S. Provisional Application Ser. No. 61/426,347 titled "Wearable Therapeutic Device," filed Dec. 22, 2010, and to U.S. Provisional Application Ser. No. 61/345,947 titled "Wearable Therapeutic Device," filed May 18, 2010, each of which are incorporated herein by reference in their entireties.

BACKGROUND OF THE INVENTION

1. Field of Invention

At least one embodiment of the present invention relates generally to a wearable therapeutic device, and more specifically, to a wearable therapeutic device configured to deliver an electric shock to a subject.

2. Discussion of Related Art

Cardiac arrest and other cardiac health ailments are a major cause of death worldwide. Various resuscitation efforts aim to maintain the body's circulatory and respiratory systems during cardiac arrest in an attempt to save the life of the victim. The sooner these resuscitation efforts begin, the better the victim's chances of survival. These efforts are expensive and have a limited success rate, and cardiac arrest, among other conditions, continues to claim the lives of victims.

SUMMARY OF THE INVENTION

Aspects and embodiments of the present invention are directed to a wearable therapeutic device with an external defibrillator. The wearable device includes therapy electrodes that are configured to administer an electric shock to a subject. The wearable device also houses receptacles proximate to the therapy electrodes. A control system bursts the receptacles to release a conductive fluid. The conductive fluid, when released from its receptacle, covers at least part of a surface of at least one therapy electrode, reducing the impedance between that therapy electrode and the subject's skin. Responsive to a cardiac event, the wearable device delivers an electric shock to the subject via the therapy electrode and conductive fluid.

At least one aspect is directed to a wearable therapeutic device. The wearable therapeutic device includes a garment that can be configured to contain an external defibrillator. The garment includes a belt configured to house at least one of an alarm module and a monitor. The belt is configured to house a first therapy electrode and a second therapy electrode. The belt is also configured to releasably receive a receptacle proximate to at least one of the first therapy electrode and the second therapy electrode, and to electrically couple the receptacle with the garment. The receptacle houses a conductive fluid.

At least one other aspect is directed to a wearable therapeutic device. The wearable therapeutic device includes a first therapy electrode and a second therapy electrode. The first and second therapy electrodes are configured to be electrically coupled to an external defibrillator. The wearable therapeutic device includes a garment configured to house the first therapy electrode and the second therapy electrode. The garment can releasably receive a receptacle configured to store a conductive fluid in a location proximate to at least one of the first therapy electrode and the second therapy electrode.

At least one other aspect is directed to a method of facilitating care of a subject. The method includes an act of providing a wearable therapeutic device configured to contain an external defibrillator. The wearable therapeutic device has a garment configured to house a first therapy electrode and a second therapy electrode. The garment is further configured to releasably receive a receptacle proximate to at least one of the first therapy electrode and the second therapy electrode to electrically couple the receptacle with the wearable therapeutic device. The receptacle is configured to house a conductive fluid. The garment can include a belt.

In some embodiments, an induction coil is configured to electrically couple the receptacle with the garment. A first winding of the induction coil can be disposed in the belt, and a second winding of the induction coil can be disposed in the receptacle. In one embodiment, a connector can electrically couple the receptacle with the garment. In one embodiment, the wearable therapeutic device includes two rear therapy electrodes and one front therapy electrode, and the belt includes one receptacle disposed proximate to each of the two rear therapy electrodes and the front therapy electrode. Each receptacle contains at least one dose of conductive fluid. A receptacle control unit can release the doses of conductive fluid from each receptacle onto its associated therapy electrode. In one embodiment, the receptacles are disposed in the wearable therapeutic device's belt and electrically coupled with the receptacle control unit. In one embodiment the receptacle control unit is contained on exactly one receptacle where it can control the operation of that one receptacle and other receptacles via electrical communication. The receptacle control unit may be an integral part of one or more than one receptacle. The receptacle can include a battery, a plurality of doses of conductive fluid, a pressure sensor, and a receptacle control unit.

In one embodiment, one receptacle control unit controls the release of conductive fluid from more than one receptacle onto more than one therapy electrode. The receptacle control unit can be housed in the belt proximate to the first therapy electrode. The receptacle control unit may also be housed proximate to other therapy electrodes, or distal from therapy electrodes. In some embodiments, at least one of the first therapy electrode and the second therapy electrode include conductive thread sewn into the garment. The therapy electrodes may include only conductive thread, or conductive thread as well as further conductive elements. In some embodiments, the conductive thread forms a stitched pattern in the garment that includes at least one of a quadrilateral shape, a polygonal shape, a circular shape, an oval shape, a round shape, an oblong shape, and a triangular shape. The conductive thread can form a stitched pattern in the garment that includes at least two substantially parallel stitched lines. In one embodiment, the belt includes conductive thread configured to electrically couple the receptacle with at least one of the first therapy electrode and the second therapy electrode. In some embodiments, at least one therapy electrode includes conductive thread facing toward the receptacle and away from a subject wearing the device.

In one embodiment, the garment includes an elastic tension member configured to hold the receptacle proximate to at least one of the first therapy electrode and the second therapy electrode. The belt can include an elastic material configured to hold the receptacle proximate to at least one of the first therapy electrode and the second therapy electrode. The belt can include a breathable fabric. At least one of the first therapy electrode and the second therapy electrode can include conductive thread sewn into the breathable fabric. In one embodiment, the belt is removably attached to the garment.

In some embodiments, the first therapy electrode is disposed in a first pocket of the garment and the second therapy electrode is disposed in a second pocket of the garment. The first or second pocket can include conductive thread sewn into the garment. The garment can include a sensing electrode, and the sensing electrode can include conductive thread sewn into the garment. In one embodiment, the first and second therapy electrodes are integral parts of the belt. The first and second therapy electrodes can also be encased within the garment. The first and second therapy electrodes can include a dry non-adhesive electrode.

In one embodiment, the garment has or can connect with at least one of a shoulder strap and a holster, and at least one of the alarm module, the monitor, and the external defibrillator are disposed in the shoulder strap or the holster. The monitor can be configured to indicate that the receptacle is absent from the belt or improperly inserted into the belt. The monitor can also indicate a need to replace the receptacle, that the receptacle is expired, that the receptacle is approaching an expiration date, that the receptacle has a fault condition, or that the receptacle has expelled at least some of the conductive fluid. In one embodiment, at least one magnet is disposed in the garment. The garment includes a conductive pad proximate to the magnet, and the conductive pad can electrically couple with a current source. The receptacle may include a contact element.

In one embodiment, instructions to operate the wearable therapeutic device are provided. The instructions include at least one instruction directing the subject to dispose the receptacle proximate to at least one of the first therapy electrode and the second therapy electrode. The instructions may also include instructions to direct the subject to interface with a user interface to prevent the delivery of an electric shock to the subject.

Other aspects, embodiments, and advantages of these exemplary aspects and embodiments are discussed in detail below. Both the foregoing information and the following detailed description are illustrative examples of various aspects and embodiments, and are intended to provide an overview or framework for understanding the nature and character of the claimed aspects and embodiments. The accompanying drawings are included to provide illustration and a further understanding of the various aspects and embodiments, and are incorporated in and constitute a part of this specification. The drawings, together with the remainder of the specification, serve to describe and explain the claimed aspects and embodiments.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
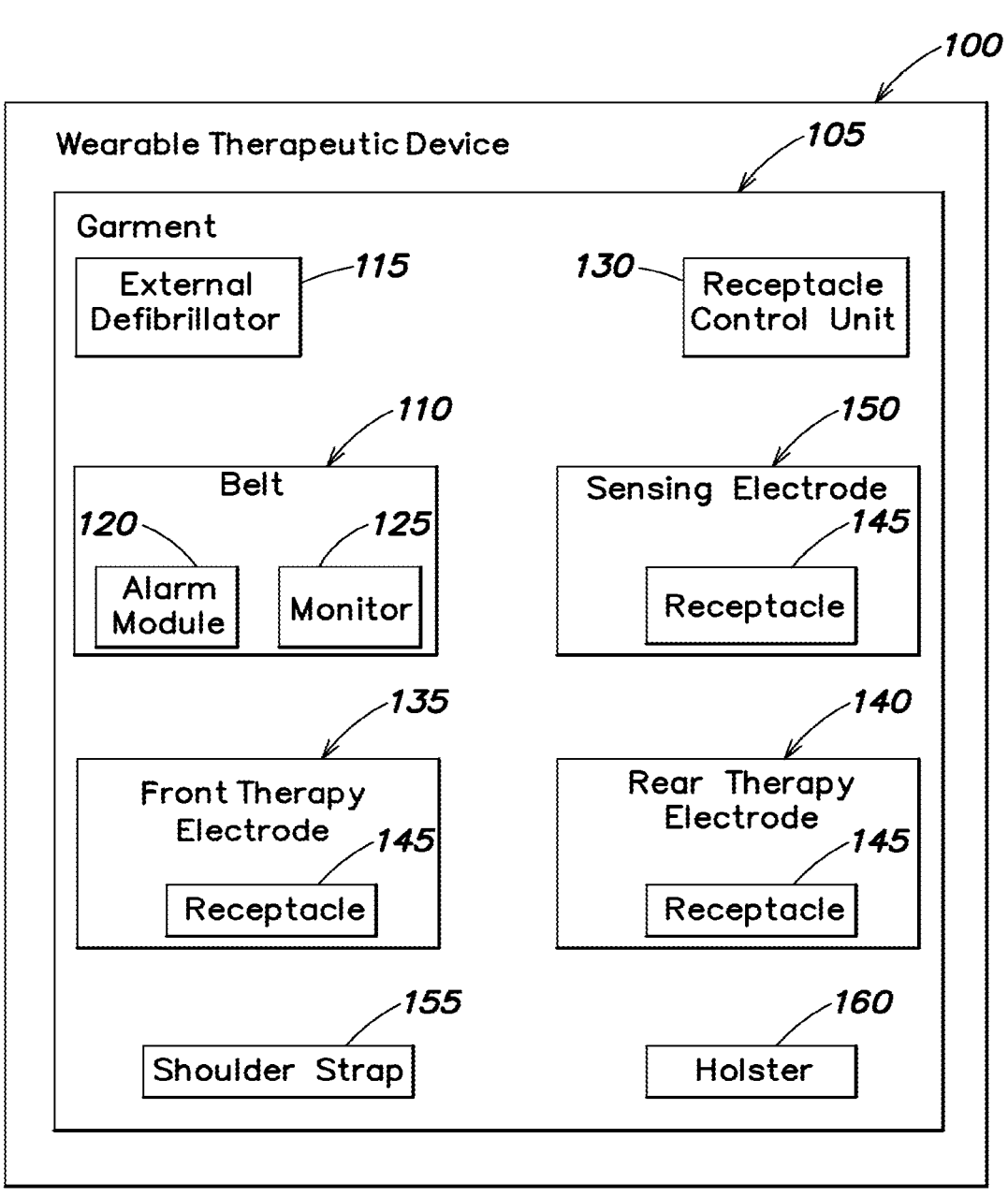
FIG. 1 is a schematic diagram depicting a wearable therapeutic device in accordance with an embodiment.

The systems and methods described herein are not limited in their application to the details of construction and the arrangement of components set forth in the description and illustrated in the drawings. The invention is capable of other embodiments and of being practiced or of being carried out in various ways. Also, the phraseology and terminology used herein is for the purpose of description and should not be regarded as limiting. The use of "including" "comprising" "having" "containing" "involving" and variations thereof herein, is meant to encompass the items listed thereafter, equivalents thereof, and additional items, as well as alternate embodiments consisting of the items listed thereafter exclusively.

Various aspects and embodiments are directed to a wearable therapeutic device. The wearable therapeutic device includes medical equipment such as an external defibrillator and at least one therapy electrode configured to deliver a shock to a subject. The wearable therapeutic device is configured to removably include at least one receptacle housing a conductive fluid. Prior to delivering an electric shock, a receptacle control unit directs the receptacle to release the conductive fluid onto at least one therapy electrode, lowering impedance between the subject's skin and the therapy electrode. After the conductive fluid is deployed, the external defibrillator administers an electric shock to the subject via the therapy electrode and conductive fluid. The therapy electrode can be housed in a belt of the wearable therapeutic device, and spent receptacles can be removed from the wearable therapeutic device and replaced with another receptacle that contains at least one dose of conductive fluid.

FIG. 1 is a schematic diagram of wearable therapeutic device 100 in accordance with an embodiment. In one embodiment, wearable therapeutic device 100 includes at least one garment 105. Garment 105 may have the shape of a vest or a shirt. In one embodiment, garment 105 includes material with a low spring rate, so that four or five different garment 105 sizes accommodate a wide range of subject body sizes, (e.g., from a 26 to 56 inch chest circumference), and each size can accommodate a 5 to 6 inch subject chest circumference size differential. In one embodiment, when positioned on a subject, garment 105 exerts between 0.050 and 1.70 lb of force about the subject's rib cage. In one embodiment, garment 105 can stretch approximately 16 inches when worn by a subject. Garment 105 may also include a wicking material (e.g., microfiber, spandex nylon, or spandex polyester) to enhance subject comfort by wicking moisture such as sweat away from the subject, which can provide a cooling effect. In one embodiment, portions of garment 105 (e.g., corresponding to the subject's chest, or garment 105 components such as electrodes or receptacles) include low spring rate material; and other portions of garment 105 include a looser material to enhance subject comfort. In one embodiment, garment 105 includes the garment described in commonly owned U.S. Patent Application No. 61/481,560 titled "Patent-Worn Energy Delivery Apparatus and Techniques for Sizing Same," which was filed on May 2, 2011, and which is incorporated by reference herein in its entirety.

In one embodiment garment 105 includes at least one belt 110. Belt 110 may be worn about a subject's waist, at a higher location about the subject's chest, or at other locations between the subject's waist and shoulders. Components of wearable therapeutic device 100 can be worn under, over, or partially under and partially over a subject's clothes.

The wearable therapeutic device 100 can include at least one of the following elements: garment 105, belt 110, external defibrillator 115, alarm module 120, monitor 125, receptacle control unit 130, first therapy electrode 135, second therapy electrode 140, receptacle 145, sensing electrode 150, shoulder strap 155, and holster 160. In one embodiment, at least one of external defibrillator 115, alarm module 120, monitor 125, receptacle control unit 130, first therapy electrode 135, second therapy electrode 140, receptacle 145, sensing electrode 150, shoulder strap 155, and holster 160 are included in or attached to belt 110. For example, at least one of alarm module 120 and monitor 125 can be fitted to open or closed pockets of belt 110 or otherwise attached to belt 110 via hook and loop fasteners, straps, or sleeves that form part of belt 110. These elements may also be integrated into belt 110, and these elements may be a permanent part of belt 110, or releasable from belt 110. Wearable therapeutic device 100 may include one, more than one, or all of the above mentioned elements, as well as additional elements.

In one embodiment, external defibrillator 115 is included in garment 105. For example, external defibrillator 115 can be attached to shoulder strap 155, or disposed in holster 160. Holster 160 may attach to or be part of garment 105, shoulder strap 155, or belt 110. In one embodiment, external defibrillator 115 is electrically coupled to at least one of first therapy electrode 135, second therapy electrode 140, and sensing electrode 150. Each of electrodes 135, 140, and 150 can include at least one receptacle 145. In one embodiment, external defibrillator 115 includes the defibrillator described in commonly owned U.S. Pat. No. 6,280,461, titled "Patent-Worn Energy Delivery Apparatus," which issued on Aug. 28, 2001, and which is incorporated by reference herein in its entirety.

In one embodiment, monitor 125 or control circuitry of external defibrillator 115 monitors a subject's condition. For example, sensing electrode 150 can sense electrical activity of the subject's heart signals. When an arrhythmic event is detected, alarm module 120 can sound a warning that the subject wearing wearable therapeutic device 100 is in danger of, or is experiencing, a heart attack, cardiac arrest, or other form of cardiac distress. This warning may be audio, visual, haptic (e.g., vibrating alarm module 120) or combinations thereof. The signals sensed by sensing electrode 150 can be displayed as electrocardiograph signal on monitor 125. This and other information can be stored in memory units associated with monitor 125 or external defibrillator 115 for analysis by a doctor, rescuer, or health care provider.

In one embodiment, alarm module 120 provides an alarm that indicates that the subject will receive an electric shock from external defibrillator 115 delivered by at least one of first therapy electrode 135 and second therapy electrode 140 unless the subject wearing wearable therapeutic device 100 takes some action to prevent external defibrillator 115 from applying the shock. For example, alarm module 120 or monitor 125 may include a user interface having at least one button or touch screen. In this example, the subject can depress at least one button. This indicates that the subject is conscious. In this example, the shock will not be applied while the subject depresses the button for a sufficient amount of time, or until control logic of external defibrillator 115 determines that the electrical heart activity of the subject (as detected by sensing electrode 150) has returned to normal. Continuing with this example, if the subject loses consciousness, the subject will release the buttons and external defibrillator 115 will apply a shock via at least two electrodes, such as any of first therapy electrodes 135 or second therapy electrodes 140. In one embodiment, first therapy electrode 135 includes at least one front therapy electrode positioned in garment 105 in front (e.g., anterior or about the chest) of the subject, and second therapy electrode 140 includes at least one therapy electrode positioned in garment 105 at the rear (e.g. posterior or about the back) of the subject. Other anterior, posterior, and lateral positioning with respect to the subject when the subject is wearing garment 105 is possible. For example, first therapy electrode 135 and second therapy electrode 140 may both be in an anterior position with respect to the subject. In one embodiment, multiple therapy electrodes are disposed in an anterior position. Multiple therapy electrodes may also be disposed in any position, e.g., anterior, posterior, or lateral.

In one embodiment, first therapy electrode 135 and second therapy electrode 140 are permanent components of wearable therapeutic device 100. Electrodes 135 and 140 can be housed anywhere in garment 105. For example, first therapy electrode 135 can be integral to garment 105 and disposed proximate to the subject's chest or abdomen when the subject is wearing wearable therapeutic device 100. Second therapy electrode 135 can be integral to garment 105 and disposed proximate to the subject's back when the subject is wearing wearable therapeutic device 100. In one embodiment, when a shock is applied, first therapy electrode 135, second therapy electrode 140, the subject's body, and external defibrillator 115 form at least part of a current path.

In one embodiment, wearable therapeutic device 100 includes at least one receptacle 145. Receptacle 145 can be housed in garment 105. For example, receptacle 145 can be disposed in belt 110, proximate to at least one of first therapy electrode 135, second therapy electrode 140, and sensing electrode 150. In one embodiment, electrodes 135, 140, and 150 are dry electrodes.

Figure 2:
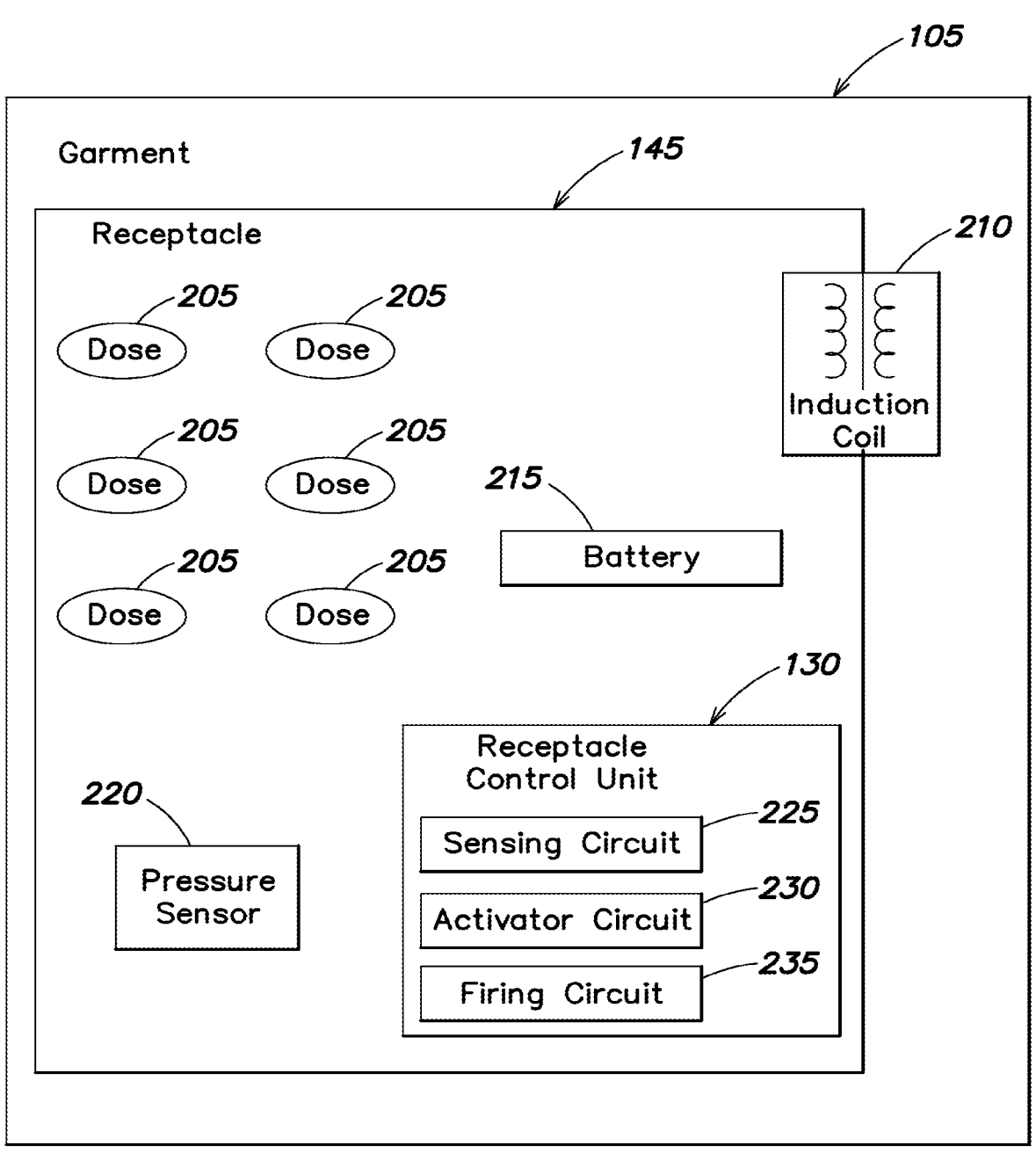
FIG. 2 is a schematic diagram depicting replaceable receptacle for a wearable therapeutic device in accordance with an embodiment.

In one embodiment, receptacles 145 are replaceable. FIG. 2 illustrates an example receptacle 145 disposed in garment 105. In one embodiment receptacle 145 is disposed in belt 110. Receptacle 145 can include at least one dose 205 of a conductive fluid, such as a gel, contained for example in a pod, pack, or capsule. Receptacle 145 can also include at least one induction coil 210, battery 215, receptacle control unit 130, and pressure sensor 220. In one embodiment, pressure sensor 220 is part of receptacle control unit 130. Receptacle control unit 130 may also include at least one sensing circuit 225, conductive fluid activator circuit 230, and conductive fluid firing circuit 235. Induction coil 210 can form an electrical connection between receptacle 145 and garment 105 including components thereof, such as first therapy electrode 135, second therapy electrode 140, or sensing electrode 150. In one embodiment, induction coil 210 includes first and second windings, with the first winding located on receptacle 145 and the second winding being located in garment 105. For example, the second winding may be a permanent fixture of garment 105 (e.g., part of belt 110) configured to form an electrical connection with the first winding of induction coil 210 located on receptacle 145 when receptacle 145 is inserted into garment 105. In one embodiment, a connector forms an electromechanical or electrical connection between receptacle 145 and garment 105. Garment 105 or elements housed therein or attached thereto such as external defibrillator 115 may include additional batteries or power sources.

In one embodiment, receptacle control unit 130 includes a circuit to control the release of conductive fluid from at least one receptacle 145. For example, receptacle control unit 130 controls current from a current source to receptacles 145 to release conductive fluid from doses 205. Receptacle control unit 130 may include a printed circuit board. The current source can be integral to or remote from wearable therapeutic device 100. For example, receptacle control unit 130 can activate the current source to provide current to receptacle 145 sufficient to deploy conductive fluid from receptacle 145. In this example, receptacle 145 may include a gas cartridge, and the current can cause the gas cartridge to ignite. Pressure from this small explosion bursts dose 205 and releases the conductive fluid. Receptacle 145 may include channels from the gas cartridge to doses 205, along which the pressure from the ignited gas travels. These channels can include polystyrene foam or other closed cell foam or semi-porous material to regulate the gas pressure.

In one embodiment, receptacle control unit 130 controls the release of conductive fluid from at least one dose 205. The released conductive fluid covers at least part of a surface of at least one of first therapy electrode 135, second therapy electrode 140, and sensing electrode 150. This conductive fluid is part of an electrical connection between the subject and at least one of electrodes 135, 140, and 150. For example, the conductive fluid lowers impedance between the subject's skin and at least one of electrodes 135, 140, and 150. In one embodiment, the conductive fluid also covers at least part of garment 105, such as part of belt 110. In one embodiment, the conductive fluid is released from receptacles 145 prior to application of a shock from one of electrodes 135 and 140 to the subject. For example, alarm module 120 can indicate a shock is imminent. When the subject does nothing to abort the impending shock, receptacle control unit 130 controls the release of conductive fluid onto at least one of first therapy electrode 135 and second therapy electrode 140, and then instructs external defibrillator 115 to administer a shock to the subject via at least two electrodes, such as first therapy electrodes 135 or second therapy electrodes 140. The conductive fluid lowers impedance between the subject and first therapy electrode 135 and second therapy electrode 140, improving the effectiveness of the shock and protecting the subject from associated burns.

In one embodiment, after the conductive fluid is released from receptacle 145, receptacle 145 can be replaced with a new receptacle 145. Receptacle control unit 130 can determine if receptacle 145 needs to be replaced. Receptacle control unit 130 can also determine if receptacle 145 is positioned properly in belt 110 or elsewhere on garment 105. Receptacle control unit 130 can also determine if receptacle 145 is properly electrically coupled with garment 105. Garment 105 or belt 110 may be soiled with conductive fluid and can be washed or cleaned after conductive fluid has been released from receptacle 145. Receptacle control unit 130 can be configured as part of one or more receptacles 145, and receptacle control unit 130 can be positioned on a single receptacle 145 and can control the release of conductive fluid from the single receptacle 145 where receptacle control unit 130 may be located as well as additional receptacles 145 that are electrically coupled to at least one of first therapy electrode 135 and second therapy electrode 140. In one embodiment, garment 105 includes two second therapy electrodes 140 and one first therapy electrode 135. In one embodiment, receptacle control unit 130 is included in or coupled to garment 105, separate from receptacles 145. In one embodiment, each receptacle 145 has its own receptacle control unit 130. In one embodiment, receptacles 145 are disposed in garment 105 proximate to at least one of first therapy electrode 135 and second therapy electrode 140. Receptacles 145 may also be disposed adjacent to at least one of first therapy electrode 135 and second therapy electrode 140. In one embodiment, receptacles 145 are disposed sufficiently close to at least one of first therapy electrode 135 and second therapy electrode 140 or sensing electrode 150 so that when the conductive fluid is released from receptacle 145 at least some of the conductive fluid contacts at least a portion of a surface of at least one of first therapy electrode 135 and second therapy electrode 140. The conductive fluid may also contact portions of belt 110 or garment 105. In one embodiment, at least one of first therapy electrode 135 and second therapy electrode 140 and sensing electrode 150 are permanently disposed within garment 105, for example within belt 110, and receptacles 145 are replaceably disposed within garment 105 so that they can be replaced after the conductive fluid is released. In one embodiment, at least one of first therapy electrode 135 and second therapy electrode 140 include conductive elements with at least one hole for the conductive fluid to pass through when it is released from receptacles 145.

In one embodiment, at least one of first therapy electrode 135 and second therapy electrode 140 electrode include conductive thread. In one embodiment, at least one of first therapy electrode 135 and second therapy electrode 140 includes only conductive thread. In one embodiment, at least one of first therapy electrode 135 and second therapy electrode 140 includes conductive thread as well as additional electrode components, such as a conductive element that may be stitched into garment 105 with the conductive thread.

Figure 3:
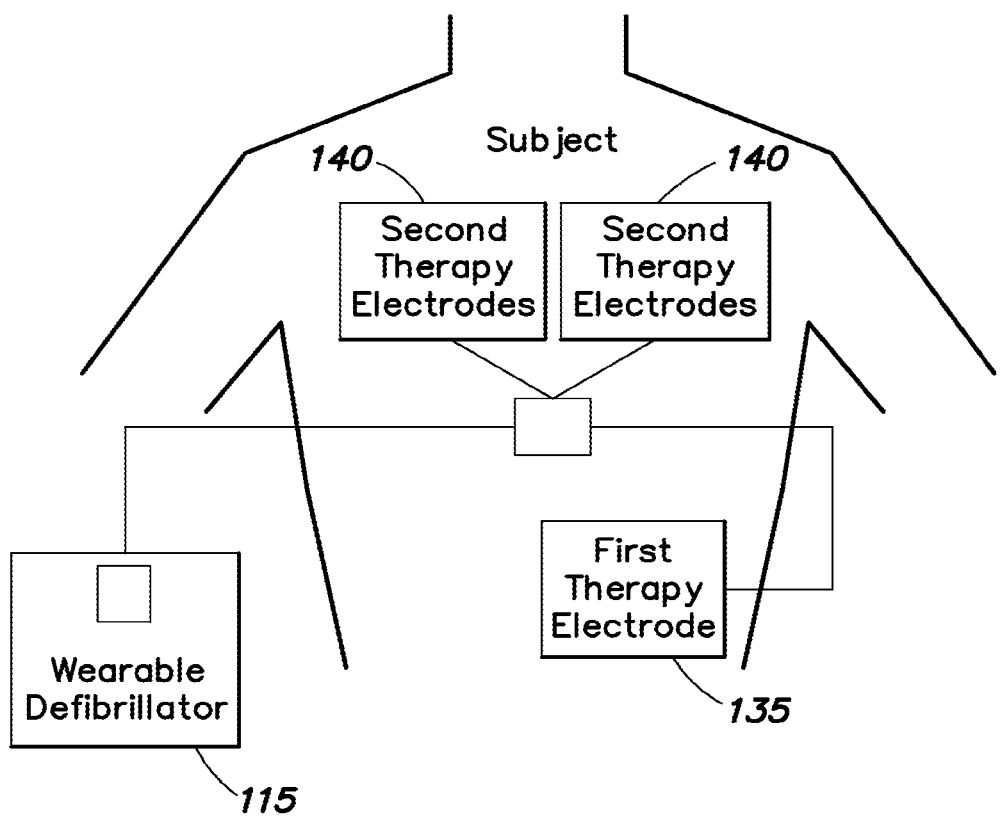
FIG. 3 is a schematic diagram depicting the therapy electrodes and external defibrillator of a wearable therapeutic device in accordance with an embodiment.

With reference to FIG. 3, in one embodiment, wearable therapeutic device 100 includes at least one of first therapy electrode 135 and second therapy electrode 140 to deliver defibrillating energy, e.g. a shock, to a subject experiencing cardiac arrhythmias or other cardiac event. In one embodiment, there is a single first therapy electrode 135 configured in garment 105 as a front electrode proximate to the front (e.g., chest side) of the subject's torso, with two second therapy electrodes 140 configured in garment 105 as rear electrodes proximate to the subject's back. In one embodiment, at least one of first therapy electrode 135 and second therapy electrode 140 are dry non-adhesive electrodes inserted into garment 105 of wearable therapeutic device 100.

In one embodiment, when the subject is defibrillated, the conductive fluid of doses 205 reduces impedance between at least one of first therapy electrode 135 and second therapy electrode 140 (or conductive thread, metallic surfaces, or combinations thereof that form a surface of electrodes 135, 140) and the subject's skin. The impedance reduction when doses 205 are released from receptacle 145 improves the efficiency of energy delivery from external defibrillator 115 to the subject and reduces the chance of skin damage in the form of, for example, burning, reddening, or other types of irritation to the skin.

Figure 4:
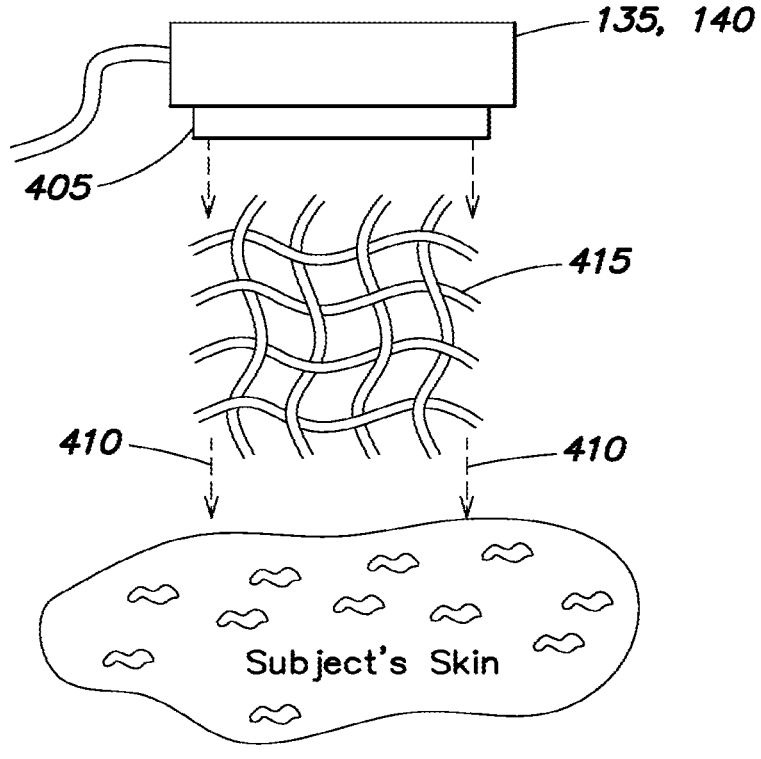
FIG. 4 is a schematic diagram depicting the interface of the therapy electrodes and the subject's skin in accordance with an embodiment.

FIG. 4 depicts an example of conductive fluid entering the area between at least one of first therapy electrode 135 and second therapy electrode 140 and the subject's skin. Conductive fluid may also be similarly disposed between sensing electrode 150 and the subject's skin. In one embodiment, conductive fluid enters the area between conductive surface 405 of electrode 135 or 140 and the subject's skin and forms a conduction path 410 from electrode 135 or 140 to the subject's skin. The conductive fluid can cover conductive thread or mesh fabric 415 that is part of garment 105 and portions of which can be disposed between subject's skin and electrode 135 or 140.

In one embodiment, after the conductive fluid has been deployed to facilitate treatment, receptacles 145 can be replaced without replacing additional garment 105 components, such as belt 110. For example, belt 110 need not be replaced, and soiled areas of belt 110 can be cleaned. As a result the subject need not wait for a replacement belt 110, and need not manually add conductive fluid to electrodes 135, 140 to maintain an appropriate electrical connection as a precaution in case additional treatment (e.g., shocks) become necessary while waiting for a replacement belt.

In one embodiment, permanently housing at least one of first therapy electrode 135 and second therapy electrode 140 in belt 110 (or elsewhere in wearable therapeutic device 100) ensures that they are properly inserted and configured to deliver a shock to the subject because the subject cannot, in this example, tamper with their location or configuration, or accidentally improperly insert them into belt 110 (e.g., backwards, not properly electrically coupled, or facing the wrong way). In one embodiment, at least one surface or a pad associated with at least one of first therapy electrode 135 and second therapy electrode 140 faces the subject's skin to make a sufficient low impedance current path between at least one of first therapy electrode 135 and second therapy electrode 140 and the subject's skin when the conductive fluid is deployed. For example, first therapy electrode 135 or second therapy electrode 140 can be housed in a pocket of garment 105, with a surface or side wall of garment 105 between the subject's skin and electrode 135 or electrode 140 having a metallic mesh pattern. The metallic mesh can include silver or other conductive metals to lower impedance between the subject's skin and the conductive surface of electrode 135 or electrode 140.

In one embodiment, at least one of first therapy electrode 135 and second therapy electrode 140 are part of or integral to at least one of wearable therapeutic device 100, garment 105, or belt 110, with doses 205 and a deployment mechanism configured in replaceable receptacle 145.

Figure 5:
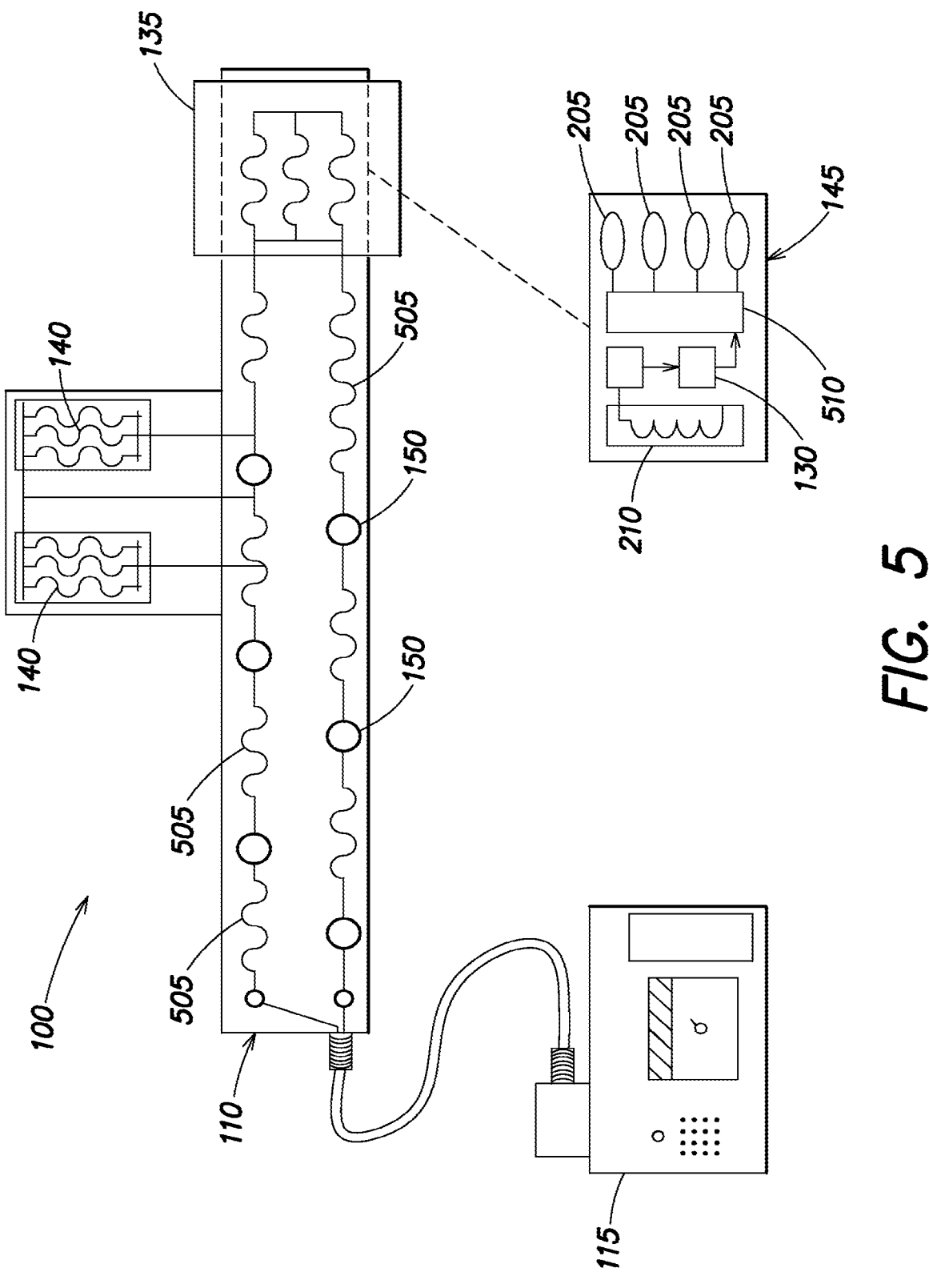
FIG. 5 is a schematic diagram depicting components of a wearable therapeutic device in accordance with an embodiment.

FIG. 5 illustrates components of wearable therapeutic device 100 according to one embodiment, with sensing electrode 150 including at least one EKG (or ECG) electrocardiogram sensor, conductive thread 505 woven into belt 110 of garment 105, and receptacle 145 disposed proximate to first therapy electrode 135 in belt 110.

In one embodiment, receptacle control unit 130 instructs receptacle 145 to release at least one dose 205 of conductive fluid. The released conductive fluid reduces impedance between the subject's skin and at least one of first therapy electrode 135 and second therapy electrode 140. External defibrillator 115 applies treatment (e.g., a shock) to the subject via at least one of first therapy electrode 135 and second therapy electrode 140. During treatment, current follows a path between the subject's skin and at least one of first therapy electrode 135 and second therapy electrode 140, via the conductive fluid. In one embodiment, after treatment, the subject removes and discards or recycles the spent receptacles 145, washes any soiled areas of garment 105, such as portions of belt 110, and installs replacement receptacles 145. The subject or wearable therapeutic device 100 may carry spare receptacles 145. In one embodiment, the subject may wear a backup wearable therapeutic device 100 during this changeover period.

In one embodiment wearable therapeutic device 100 indicates to the subject whether or not receptacles 145 have been properly inserted. For example, audio, visual, or haptic signals, or combinations thereof, can be provided by alarm module 120 or monitor 125. By incorporating at least one of first therapy electrode 135 and second therapy electrode 140 and associated wiring into wearable therapeutic device 100, garment 105 is more comfortable for the subject wearing it. There are fewer components to assemble and maintain, and to cause subject discomfort during use.

In one embodiment, receptacles 145 are replaceable subunits of garment 105. The subject can be supplied with spare receptacles 145 so that spent or consumed receptacles 145 can be quickly replaced in the event of their use during treatment, providing continuous or essentially continuous protection without having to replace belt 110, electrodes 135 or 140, or other wearable therapeutic device components.

Receptacle 145 may also include gel delivery mechanism 510, receptacle control unit 130 to control conductive fluid delivery and to communicate with external defibrillator 115, and conduction coil 210 (or other interface such as a connector) to interface with garment 105. In one embodiment, receptacle control unit 130 controls gel delivery mechanism 510 to release a charge. The charge bursts a capsule that includes at least one dose 205, releasing conductive fluid.

Figure 6:
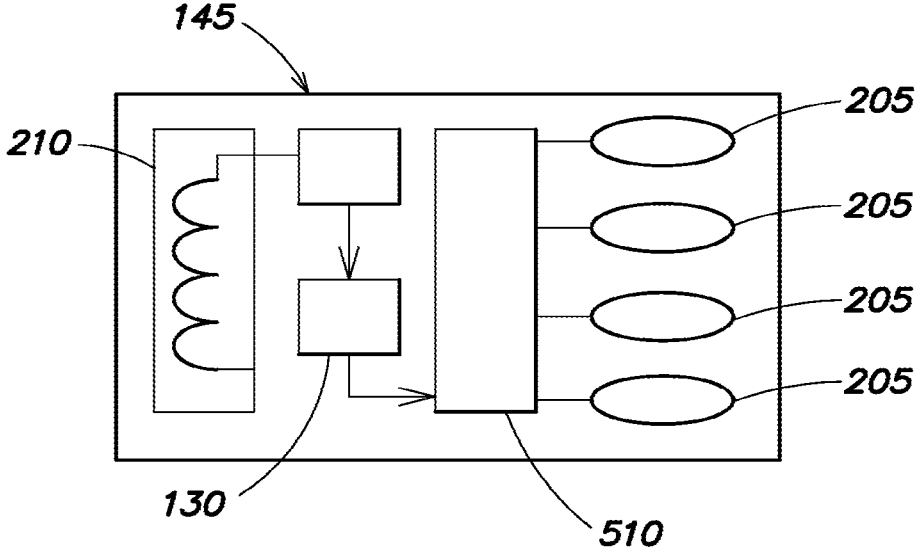
FIG. 6 is a schematic diagram depicting a receptacle of a wearable therapeutic device in accordance with an embodiment.

FIG. 6 depicts receptacle 145 in accordance with an embodiment. In one embodiment, receptacle 145 includes doses 205 of conductive fluid, such as an impedance reducing gel. In one embodiment, receptacle 145 includes a plurality of doses 205 of conductive fluid contained in packs or pods within receptacle 145. In one embodiment, at least one of first therapy electrode 135 and second therapy electrode 140 are formed by conductive thread (e.g., wires or other conductive material) either disposed in or sewn into garment 105. First therapy electrode 135 and second therapy electrode 140 can include conductive thread encased within garment 105 (for example within belt 110). In one embodiment, the conductive thread is positioned within garment 105 between the subject and first therapy electrode 135 or second therapy electrode 140 to afford the patient an increased level of comfort while wearing wearable therapeutic device 100. For example, at least a portion of garment 105 can be disposed between conductive thread 505 and the subject so that conductive thread 505 does not directly contact the subject.

Figure 7:
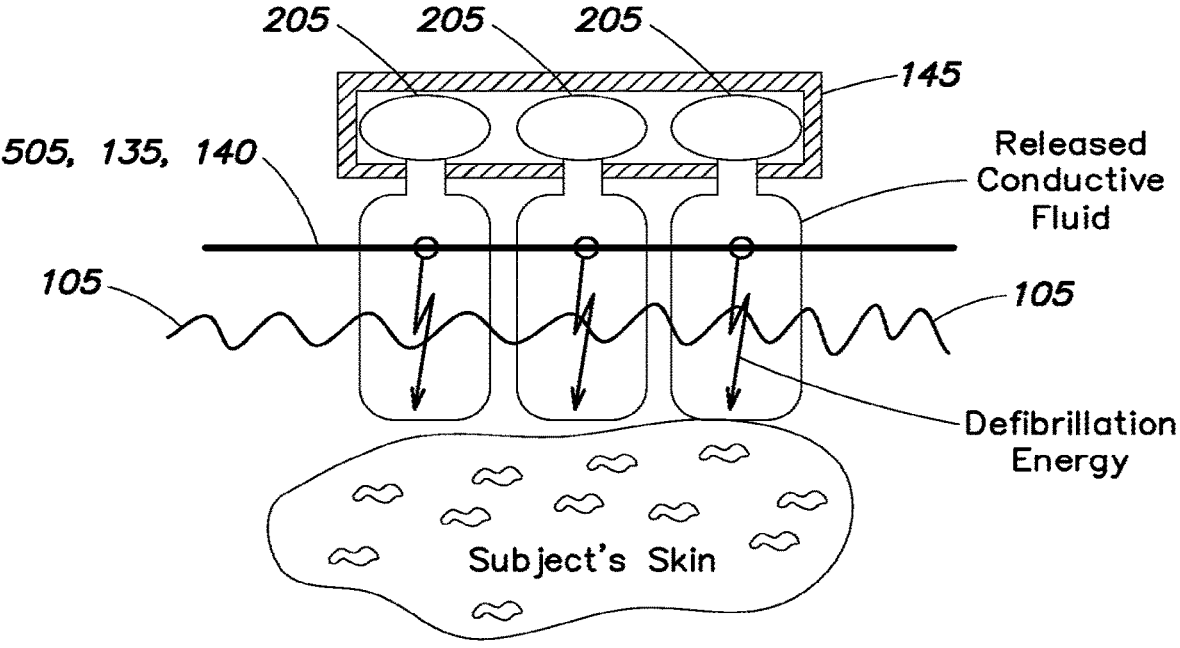
FIG. 7 is a schematic diagram depicting a receptacle of a wearable therapeutic device in accordance with an embodiment.

FIG. 7 illustrates conductive fluid release from doses 205 in one embodiment. For example, the conductive fluid delivery mechanism (e.g., at least one of receptacle control unit 130, sensing circuit 225, activator circuit 230, firing circuit 235, and pressure sensor 220) cause the conductive fluid to release from their containment capsules, pods, or packs and flow between at least one of therapy electrodes 135 and 140 through garment 105 (e.g., a metallic mesh fabric) and onto the subject's skin, reducing impedance between electrodes 135, 140, and the subject's skin. In one embodiment, at least one of therapy electrodes 135, 140 are formed by conductive material such as conductive thread 505 sewn, integrated, or disposed into garment 105. In one embodiment, at least one of therapy electrodes 135, 140 are formed entirely or essentially entirely of conductive thread 505. In one embodiment, at least one of therapy electrodes 135, 140 include conductive thread 505 and additional conductive elements, such as a metal plate.

In one embodiment, the conductive fluid includes a gel, liquid, or other material that lowers impedance for energy transfer between electrodes 135, 140, and the subject. The conductive fluid can remain on the subject's skin for a period of time such as several hours before it is removed, and the conductive fluid remains functional as an impedance reducing material during this time period. The conductive fluid in one embodiment also has sufficient shelf life to remain dormant for a period of time prior to use. In one embodiment, receptacle 145 indicates an expiration date of the conductive fluid. Receptacle control unit 130 can determine the expiration date and upon or prior to expiration indicates via alarm module 120 or monitor 125 that receptacle 145 should be replaced.

Figure 8:
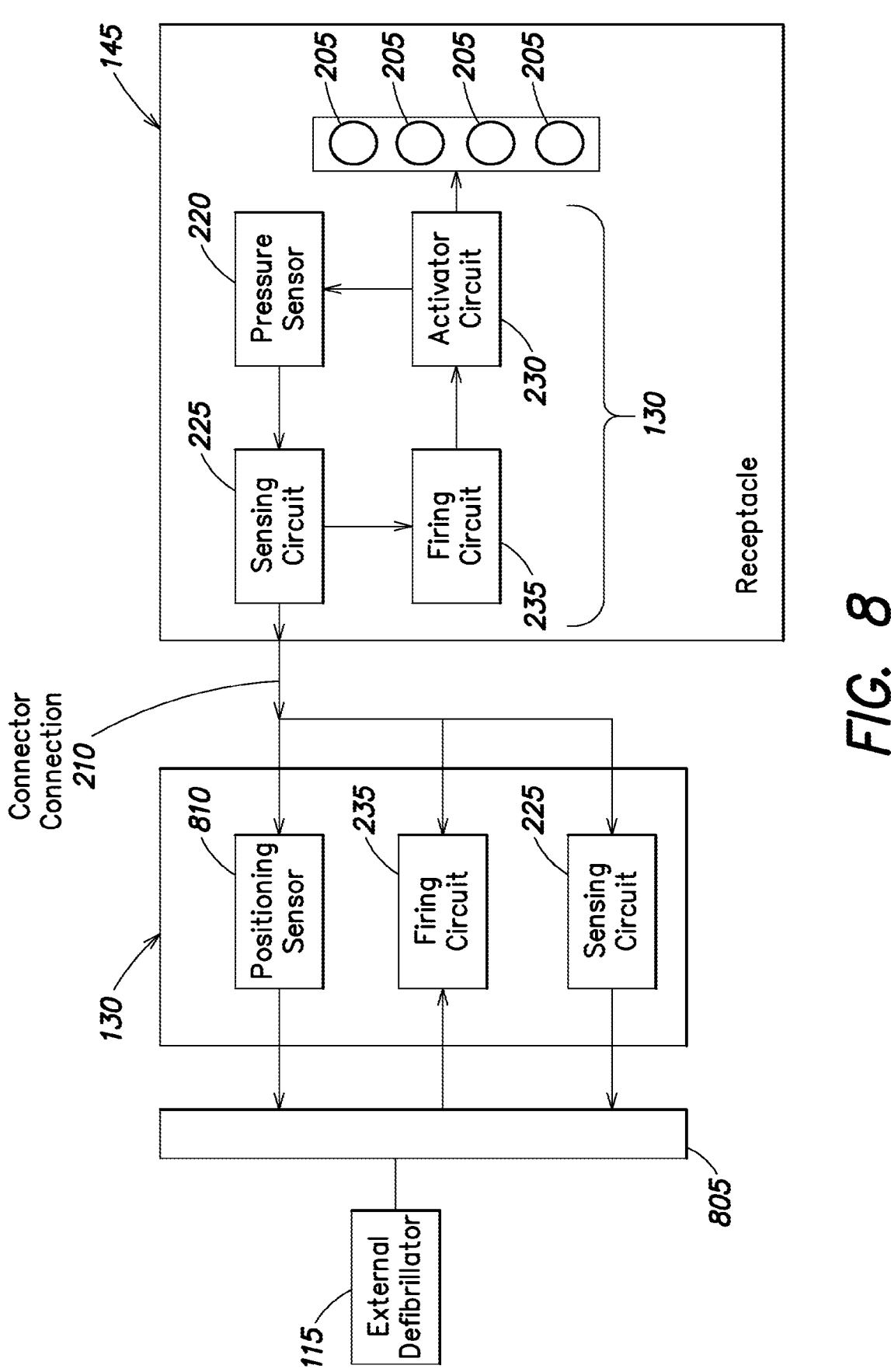
FIG. 8 is a schematic diagram depicting communication between a receptacle of the wearable therapeutic device and an external defibrillator of the wearable therapeutic device in accordance with an embodiment.

In one embodiment, receptacle 145 includes receptacle control unit 130 to communicate with external defibrillator 115 to release the conductive fluid at the appropriate time. Information communicated between the receptacle 145 and external defibrillator (via at least one receptacle control unit 130 located on receptacle 145, external defibrillator 115, garment 105, or combinations thereof) includes: the presence or absence of receptacle 145; whether or not the conductive fluid has been released from receptacle 145; a fault condition that can occur if receptacle 145 has been commanded to release the conductive fluid but the conductive fluid has failed to release; the integrity of gas chambers associated with pressure sensor 220 that are configured to deliver pressure to doses 205 to release the conductive fluid; and the age of the conductive fluid based, for example, on the date of manufacture of the conductive fluid or of receptacle 145. FIG. 8 illustrates an example of the connection between receptacle 145 and external defibrillator 115 via interface 805.

In one embodiment, pressure sensor 220 detects if pressure conduction or gas chambers within conductive fluid activator 230 have been compromised. The pressure conductor chambers can be purged such that their contents change color when exposed to air. In one embodiment, there can be a vacuum on the pressure conduction chambers of activator 230, and pressure sensor 220 detects when the chamber has been compromised based on changes in its pressure. In one embodiment, external defibrillator 115 detects when, or is informed that the conductive fluid has been released, when receptacle 145 has a fault condition, is missing, or improperly inserted, and when the conductive fluid is expired or approaching expiration. External defibrillator 115 may then indicate this status condition to the subject via its own monitor or interface, or via alarm module 120 or monitor 125, so that the subject can take the appropriate action.

With reference to FIGS. 2 and 8, among others, the connection between receptacle 145 and external defibrillator 115 via garment 105 can incorporate induction coil 210, capacitively coupled IR link, other wireless connections, magnets, or can be a hardwire connection using a connector. The connection allows receptacle 145 to be removed and replaced, for example after the conductive fluid has been released at the appropriate time during treatment.

Portions of receptacle control unit 130 can be located entirely on receptacle 145, entirely external to receptacle 145, or both on receptacle 145 and external to receptacle 145 at other locations of wearable therapeutic device 100. For example, components of any of firing circuit 235, sensing circuit 225, pressure sensor 220, positioning sensor 810, and activator circuit 230 can be part of receptacle 145, external to receptacle 145, or connected to receptacle 145 via a connector such as induction coil 210.

Figure 9:
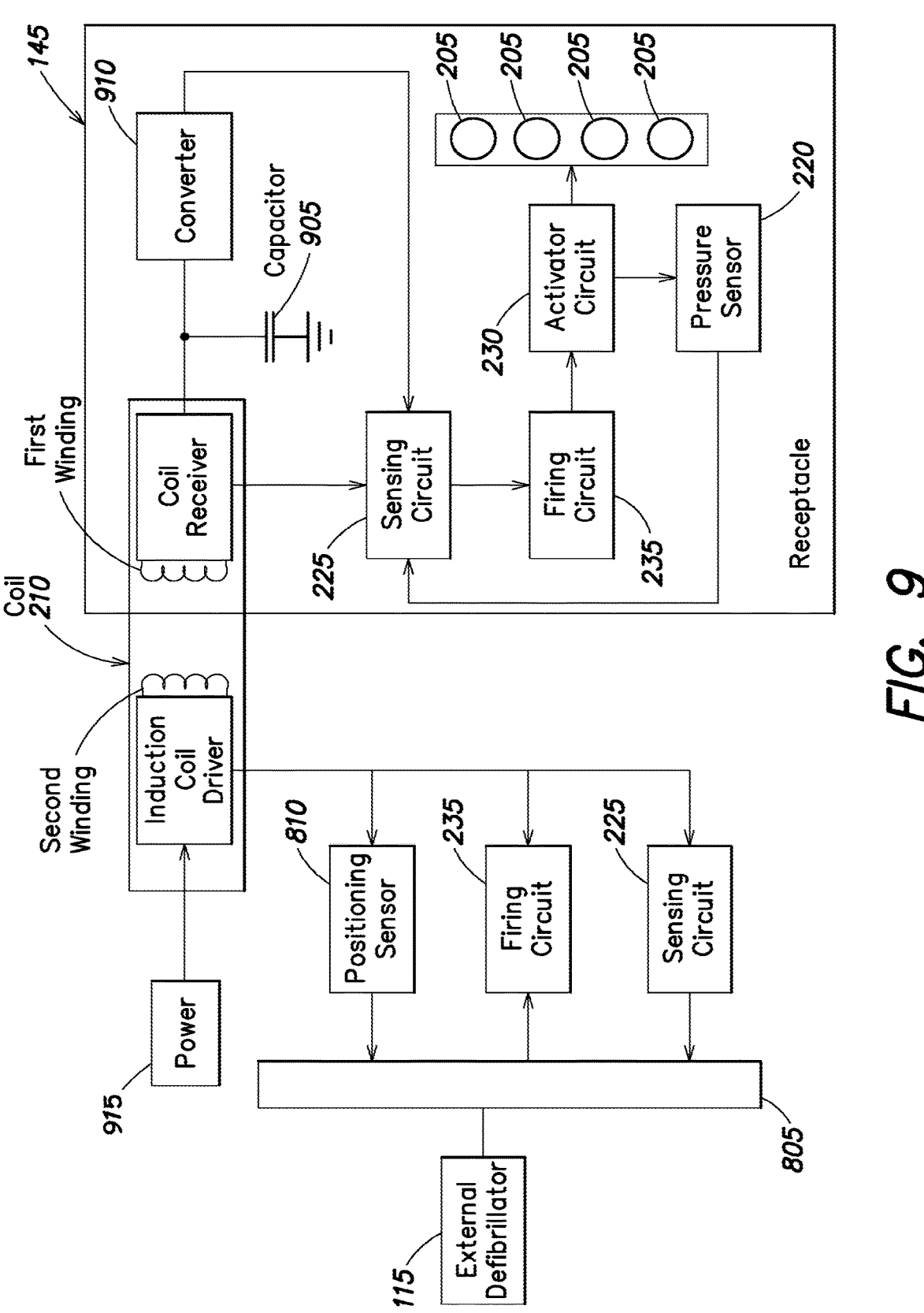
FIG. 9 is a schematic diagram depicting communication between a receptacle of the wearable therapeutic device and an external defibrillator of the wearable therapeutic device in accordance with an embodiment.
Figure 10:
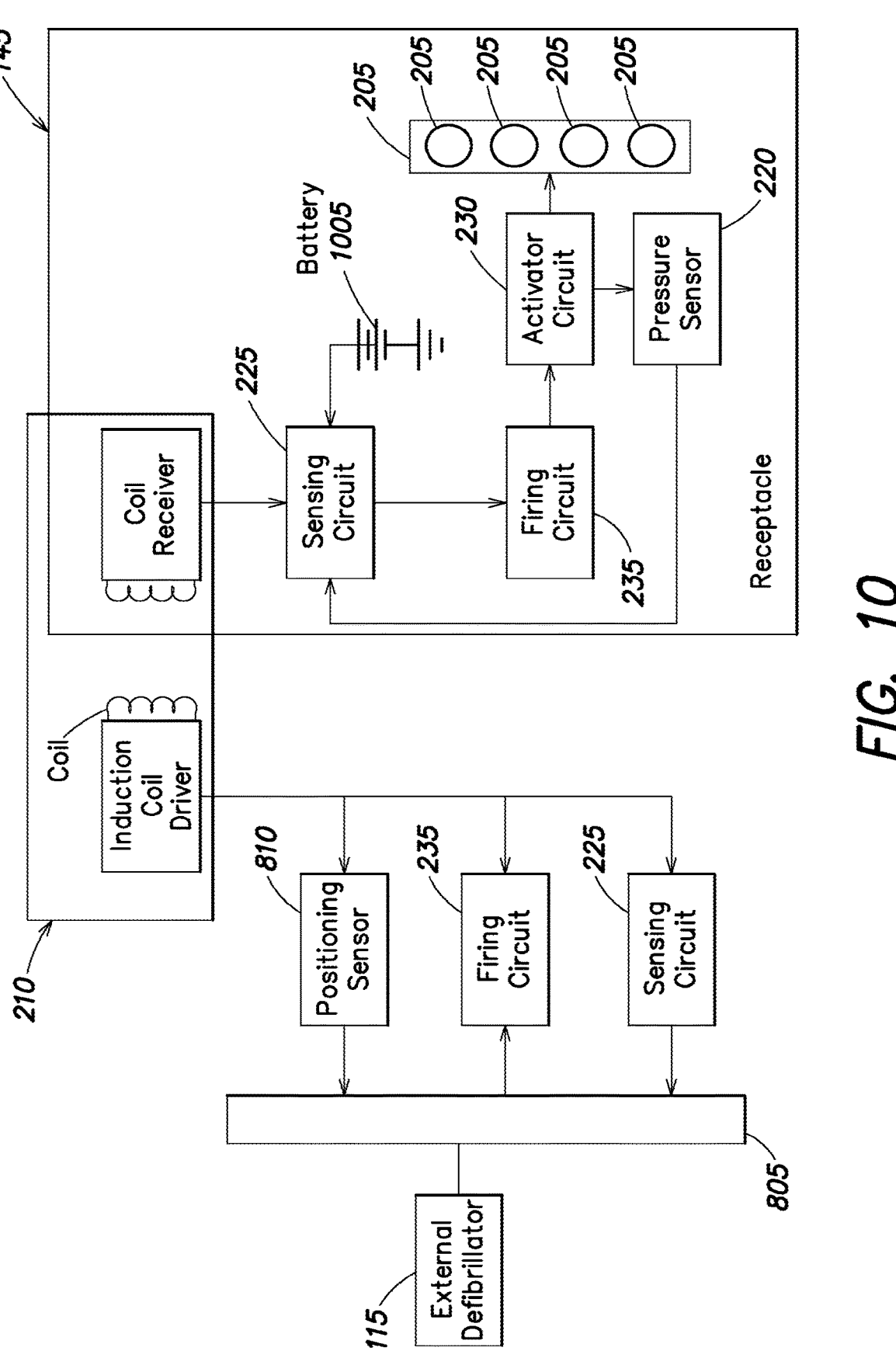
FIG. 10 is a schematic diagram depicting communication between a receptacle of the wearable therapeutic device and an external defibrillator of the wearable therapeutic device in accordance with an embodiment.

FIG. 9 depicts an example where induction coil 210 connects receptacle 145 with garment 105 and external defibrillator 115. In one embodiment, receptacle 145 electrically couples with garment 105 via at least one induction coil 210. In one embodiment, a first winding of induction coil 210 is disposed on receptacle 145 and a second winding is disposed in garment 105. When receptacle 145 is inserted into place in garment 105, the first and second windings are brought into position to form an electrical coupling between receptacle 145 and external defibrillator 115 via garment 105 and its wiring. In one embodiment, induction coil 210 permits close proximity communication and power transfer between receptacle 145 and garment 105 (and garment 105's components) without a hardwired connection via a connector. Induction coil 210 may be at least partially woven, sewn, or embroidered with conductive elements into garment 105 or components thereof such as therapy pads of electrodes 135, 140. In one embodiment, power for receptacle 145 is provided by capacitor 905, with induction coil 210 transferring power to receptacle 145 from power supply 915 to charge capacitor 905. In one embodiment, converter 910 converts AC power from power supply 915 to DC power that can be provided to any of sensing circuit 225, pressure sensor 220, activator circuit 230, firing circuit 235, or positioning sensor 810. Power for receptacle 145 can also be provided by battery 1005 as illustrated in FIG. 10.

Figure 11:
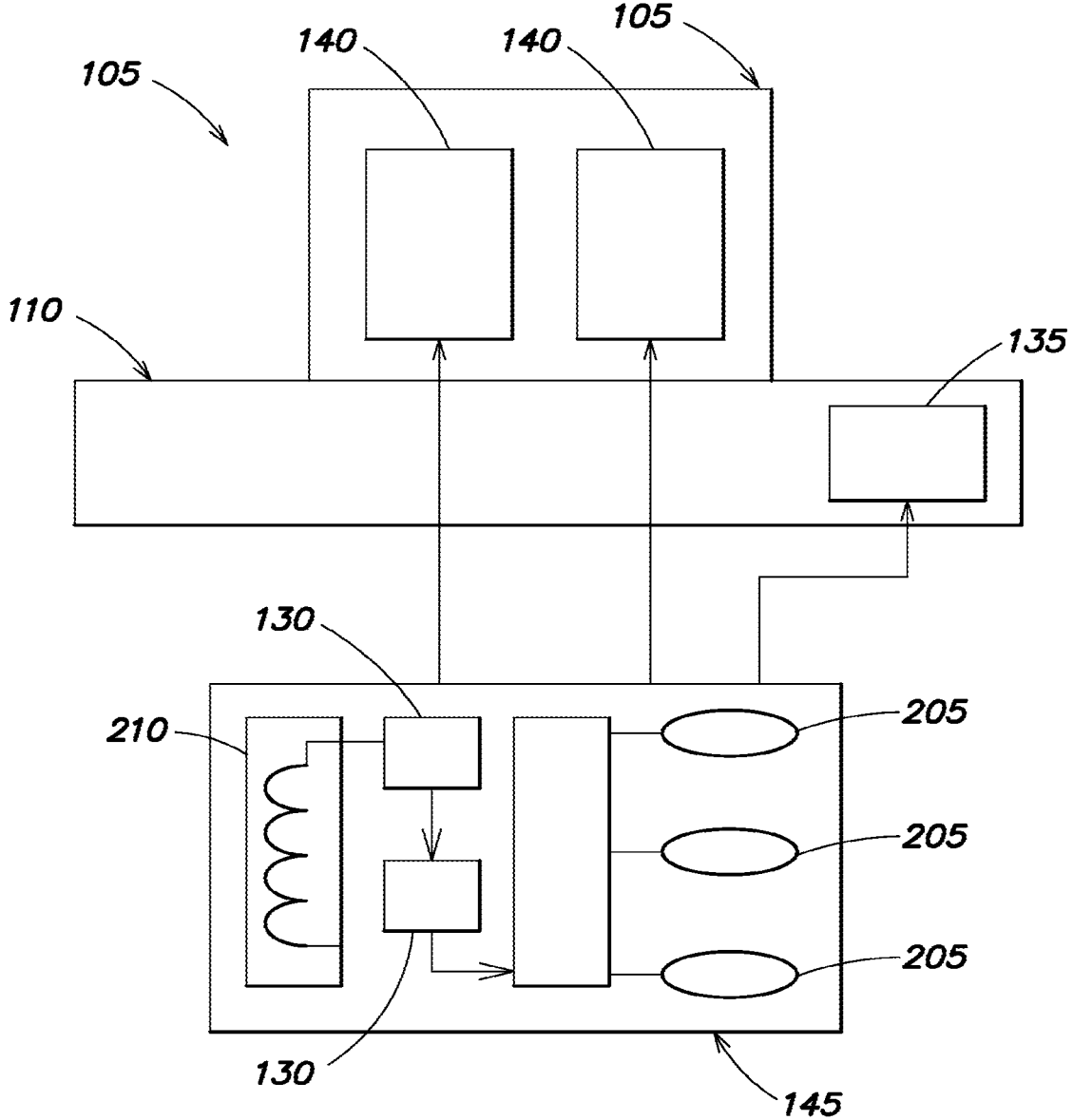
FIG. 11 is a schematic diagram depicting the wearable therapeutic device in accordance with an embodiment.

In one embodiment, receptacles 145 are packaged as individual self contained units. For example, with one first therapy electrode 135 and two second therapy electrodes 140, three receptacles 145 (one for each of the three therapy electrodes) can be identical, as illustrated in FIG. 11.

Figure 12:
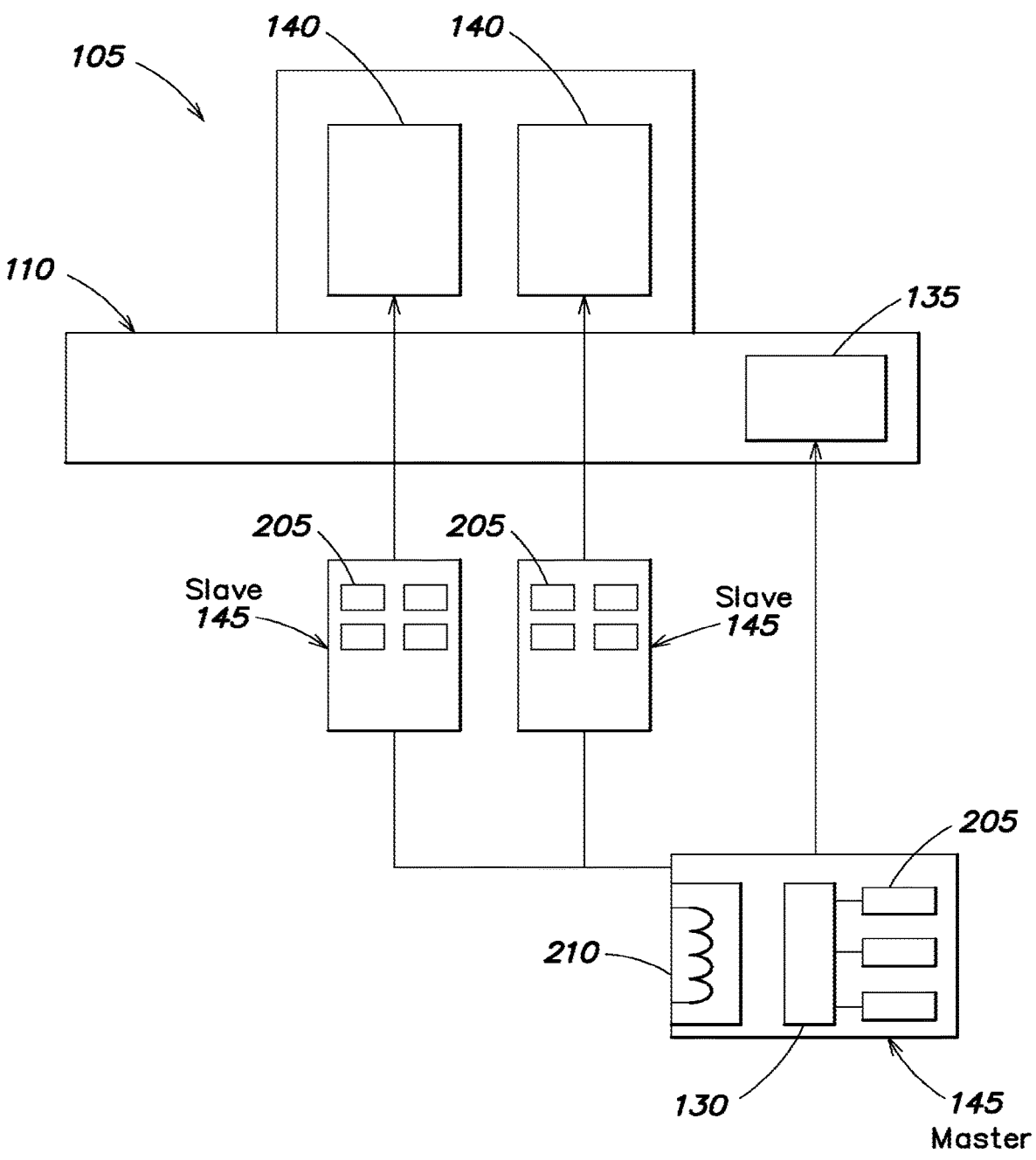
FIG. 12 is a schematic diagram depicting the wearable therapeutic device in accordance with an embodiment.

In one embodiment with one front therapy electrode 135 and two rear therapy electrodes 140, the three therapy electrodes are connected as a group, with one of the three (or other number) of therapy electrodes containing the electronics (e.g., at least part of receptacle control unit 130) and interface (e.g., connection such as induction coil 210 or hardwire connector) to connect with garment 105. In this example, the remaining two therapy electrodes are slaves to the one therapy electrode containing the electronics. After treatment, the group of three receptacles disposed proximate to their corresponding electrodes can be replaced. The master receptacle 145 can be proximate to one of front therapy electrode 135 or rear therapy electrodes 140, with the master receptacle 145 and two slave receptacles 145 in wired electrical communication with each other, as illustrated in FIG. 12.

In one embodiment, garment 105 includes conductive thread 505 to form electrical connections between areas of garment 105 and between wearable therapeutic device 100 components. First therapy electrode 135, second therapy electrode 140, and sensing electrode 150 can include conductive thread 505 or metallic surfaces sewn into garment 105. Conductive thread 505 can also provide connections between any of electrodes 135, 140, and 150 and battery powered wearable external defibrillator 115. In one embodiment, sensing electrodes 150 pick up the subject's ECG (EKG) signals and provide that signal to external defibrillator 115. Therapy electrodes 135, 140 and the conductive fluid form at least part of a current path to transfer energy from external defibrillator 115 to the subject.

Figure 14:
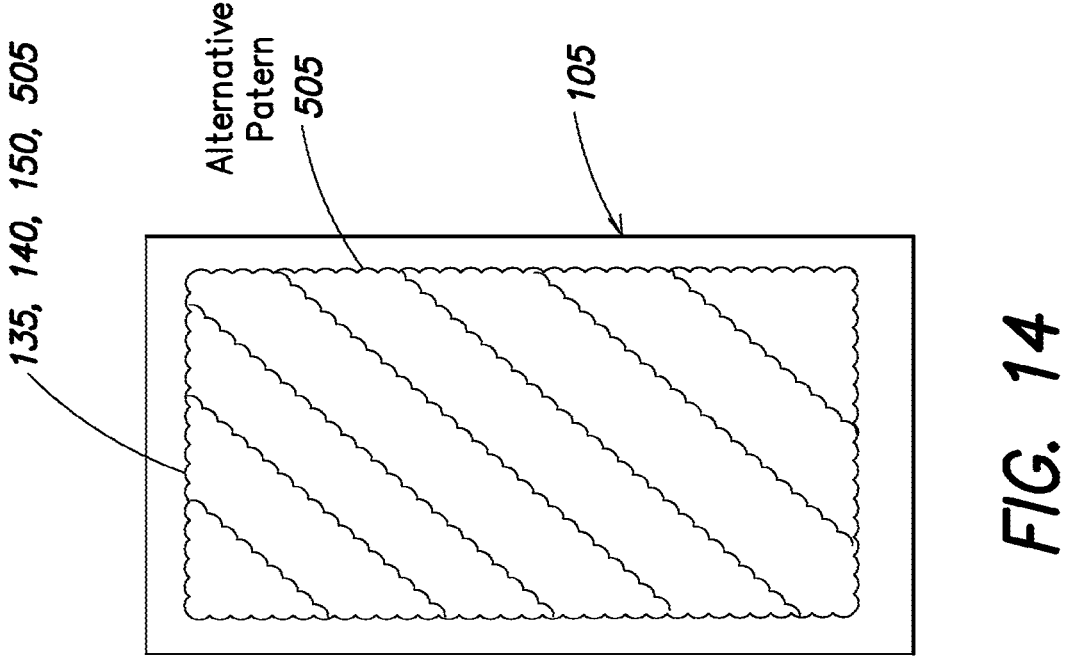
FIG. 14 is a schematic diagram depicting electrodes of the wearable therapeutic device that include conductive stitching in accordance with an embodiment.
Figure 13:
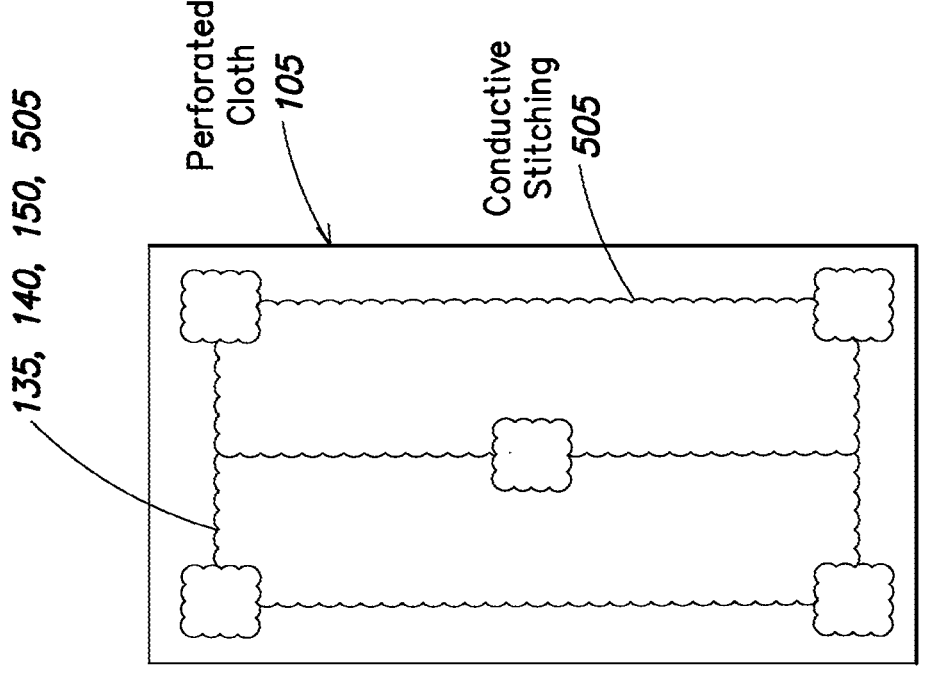
FIG. 13 is a schematic diagram depicting electrodes of the wearable therapeutic device that include conductive stitching in accordance with an embodiment.
Figure 15:
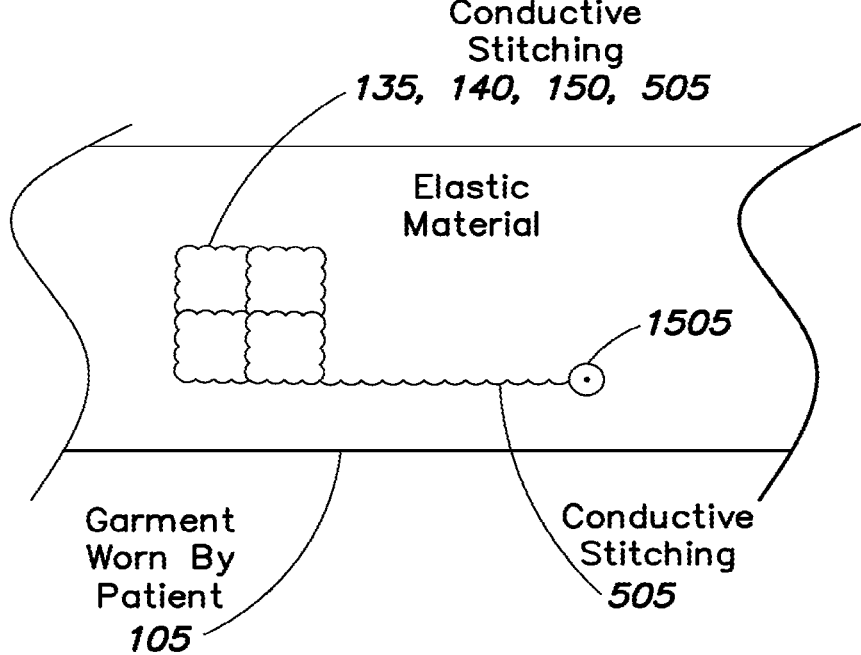
FIG. 15 is a schematic diagram depicting electrodes of the wearable therapeutic device that include conductive stitching in accordance with an embodiment.
Figure 16:
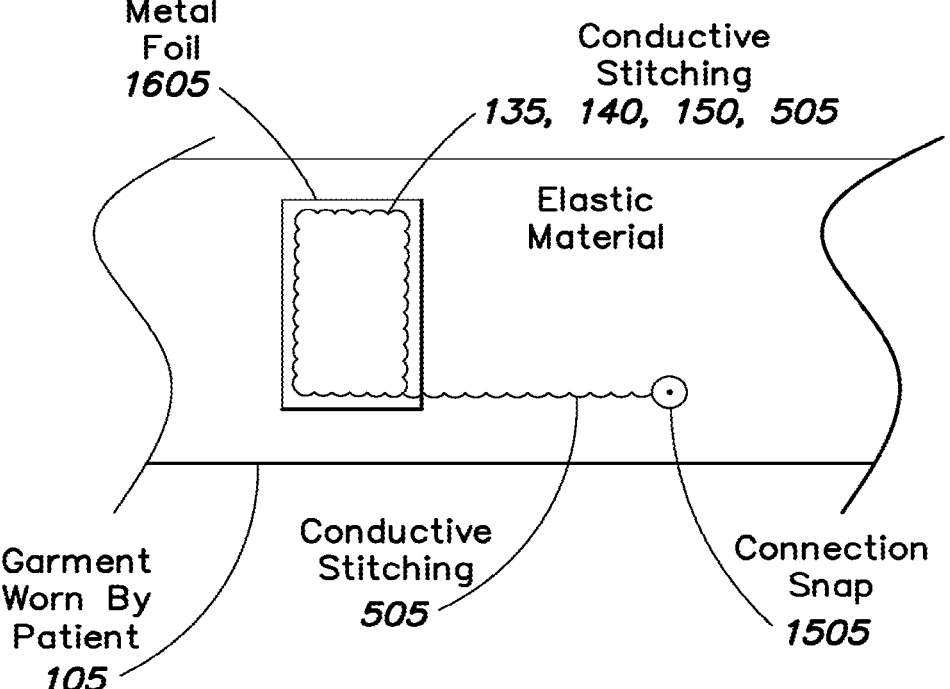
FIG. 16 is a schematic diagram depicting electrodes of the wearable therapeutic device that include conductive stitching in accordance with an embodiment.

In one embodiment, electrodes 135, 140, and 150 include conductive stitching 505 in various patterns in order to achieve proper EKG sensing and to administer therapy. Examples of this are illustrated in FIGS. 13 and 14, where the conductive stitching 505 constitutes at least one of first therapy electrode 135, second therapy electrode 140 and sensing electrode 150. In one embodiment, at least one of electrodes 135, 140, and 150 include only conductive stitching 505. Garment 105 may include an elastic material. An example of this is illustrated in FIG. 15, where connection snap 1505 can electrically couple at least one of electrodes 135, 140, and 150 with other components of wearable therapeutic device 100 such as garment 105, receptacles 145 or external defibrillator 115. In one embodiment, at least one of electrodes 135, 140, and 150 include conductive stitching 505 that holds a metal foil 1605 or other conductive component in place in garment 105. In this example, at least a portion of at least one of electrodes 135, 140, and 150 includes conductive thread 505 and metal foil 1605. An example of this is illustrated in FIG. 16.

In one embodiment, conductive thread 505 is sewn into garment 105 (e.g., belt 110) in a zigzag pattern that can stretch as part of garment 105. This stretchable conductive thread stitching 505 connects therapy electrodes 135 and 140 with receptacle control unit 130 or other garment 105 components (e.g., external defibrillator 115, receptacle 145, sensing electrode 150) in the absence of additional wires. Conductive thread (e.g., conductive wiring) 505 can face toward or away from the subject's skin. In one embodiment, conductive stitching 505 faces toward receptacle 145 and away from the subject's skin so as to not irritate the subject. When the conductive fluid releases, it contacts the conductive thread 505 and spreads through at least a portion of garment 105 and contacts the subject's skin. In one embodiment, an elastic tension member of garment 105 is positioned proximate to receptacle 145 to hold receptacle 145 in position proximate to one of electrodes 135 and 140. When conductive stitching 505 faces toward the subject's skin, electrical contact between the electrodes 135 or 140 and the subject's skin can occur in the absence of conductive fluid.

Figure 17:
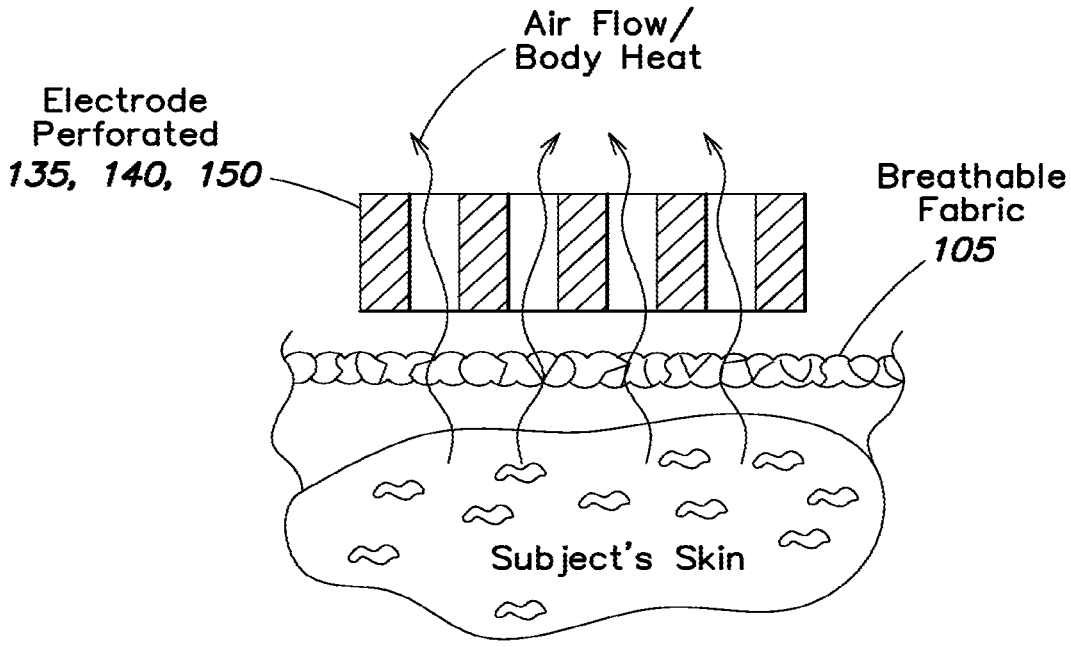
FIG. 17 is a schematic diagram depicting electrodes of the wearable therapeutic device that are perforated to enhance airflow in accordance with an embodiment.

In one embodiment, garment 105 is formed of breathable fabric, or a material that wicks heat away from the subject's body. This reduces heat buildup between therapy electrodes 135, 140 and the subject's (e.g., patient's) skin. Using conductive thread 505 for electrodes 135, 140 further reduces heat buildup in one embodiment where therapy electrodes 135, 140 are formed from conductive thread 505 in the absence of metallic foil 1605. In one embodiment, at least one of therapy electrodes 135, 140, sensing electrode 150, and receptacle 145 are made of perforated materials that allow air flow proximate to the subject's skin. This air flow can dry the skin to avoid rashes and other skin problems as a result of heat buildup and irritation. An example of this is illustrated in FIG. 17.

Figure 18:
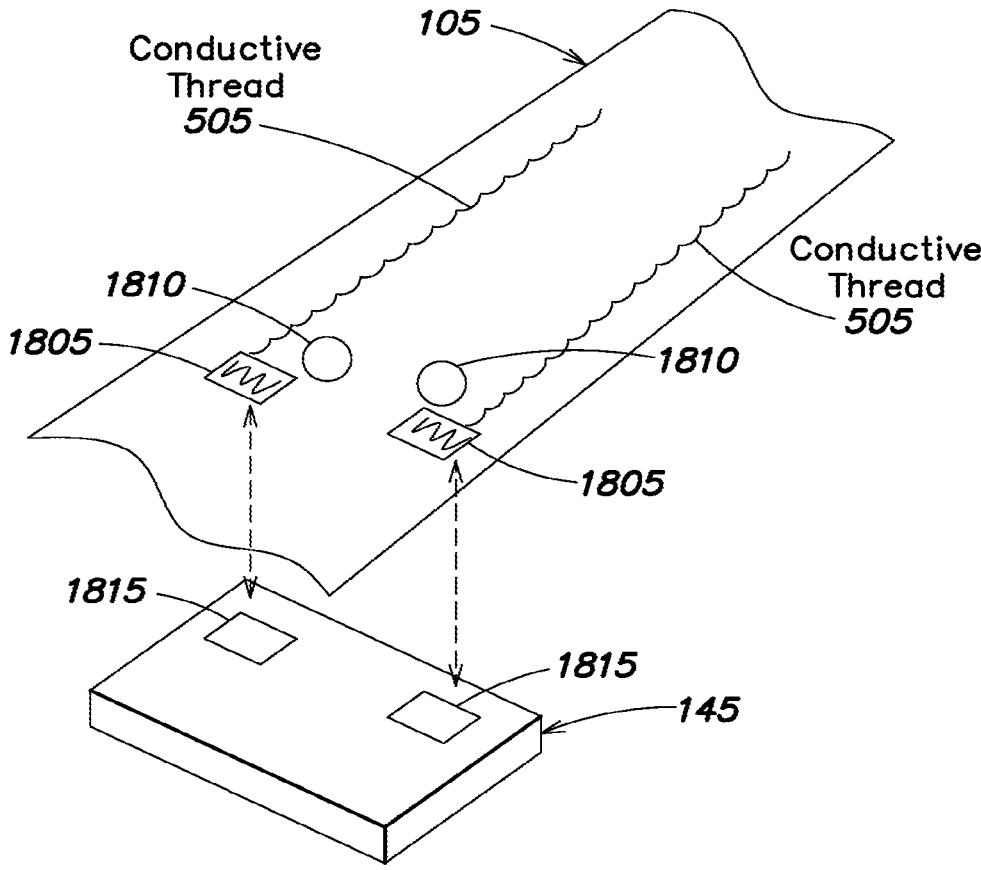
FIG. 18 is a schematic diagram depicting components of a wearable therapeutic device in accordance with an embodiment.
Figure 19:
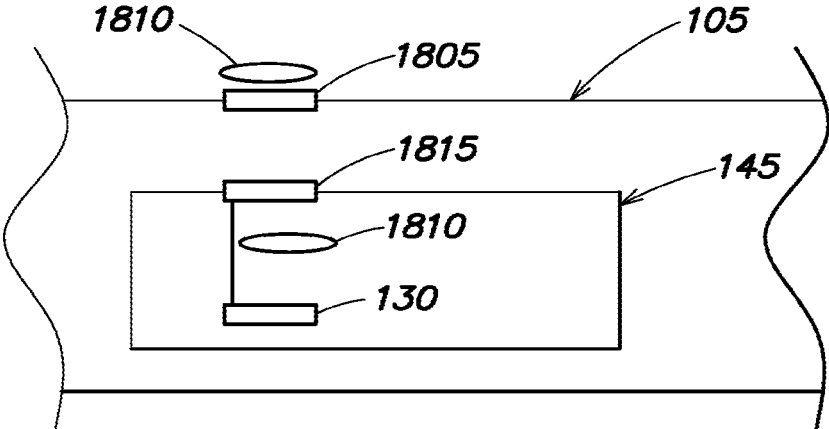
FIG. 19 is a schematic diagram depicting components of a wearable therapeutic device in accordance with an embodiment.

FIG. 18 and FIG. 19 are schematic diagrams depicting an embodiment where garment 105 includes conductive pads 1805 and magnets 1810 to align garment 105 with receptacle 145 to facilitate electrical coupling between garment 105 and receptacle 145. Conductive pads 1805 may include conductive thread 505 or other textile materials woven into garment 105 to provide current from a current source to receptacles 145. The current source can be housed within or remote from wearable therapeutic device 100. In one example, magnets 1810 are disposed proximate to conductive pads 1805. Receptacle 145 can also include magnets 1810. Magnets 1810 provide magnetic force (attractive or repulsive) between garment 105 and receptacle 145 to align conductive pads 1805 with receptacle 145. For example, attractive magnetic forces between magnet 1810 and conductive contact elements 1815 can indicate alignment between conductive pads 1805 and receptacle 145, or repulsive magnetic forces can indicate improper alignment, facilitating the insertion of receptacle 145 into garment 105. Receptacle 145 can include conductive contact elements 1815 that align with conductive pads 1805 when receptacle 145 is properly positioned in garment 105. Forces from magnets 1810 align conductive contact elements 1815 with conductive pads 1805 to provide an electrical connection between garment 105 and receptacle 145. Current may pass via this electrical connection, under control of receptacle control unit 130, to release conductive fluid from receptacles 145. In one embodiment, receptacle 145 is disposed in a pocket of garment 105, and magnets 1810 are disposed in garment 105 on opposite sides of receptacle 145 when disposed in the pocket. In one embodiment, magnets 1810 are coated, for example in plastic, to protect from wear, damage (e.g., during washing), or high moisture conditions. In one embodiment, conductive pad 1805 is at least part of electrode 135, 140, or 150.

In one embodiment, garment 105 includes snaps to align garment 105 with receptacle 145 to facilitate electrical coupling between garment 105 and receptacle 145. For example, snaps can fix garment 105 in position with contact elements 1815 aligned with conductive pads 1805.

Figure 20:
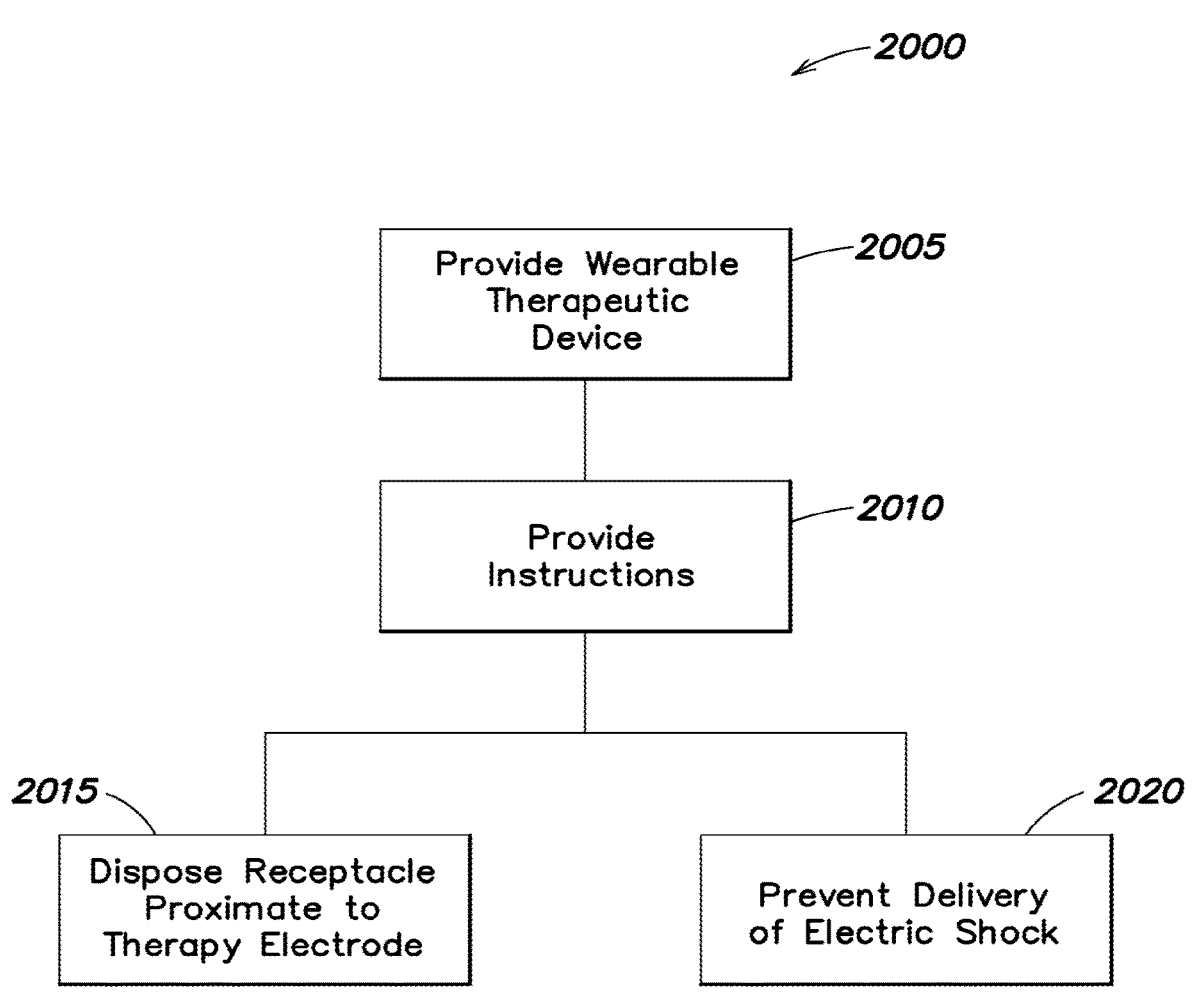
FIG. 20 is a flow chart depicting a method of facilitating care of a subject in accordance with an embodiment.

FIG. 20 is a flow chart depicting a method 2000 of facilitating care of a subject. In one embodiment, method 2000 includes an act of providing a wearable therapeutic device (ACT 2005). In one embodiment, providing a wearable therapeutic device (ACT 2005) includes providing a device configured to contain an external defibrillator and having a garment configured to permanently house a first therapy electrode and a second therapy electrode. Providing a wearable therapeutic device (ACT 2005) can also include providing a device having a garment configured to releasably receive a receptacle proximate to at least one of the first therapy electrode and the second therapy electrode. The receptacle can house a conductive fluid, and the garment can electrically couple the receptacle with the wearable therapeutic device.

In one embodiment, providing the wearable therapeutic device (ACT 2005) includes providing the wearable therapeutic device, wherein the garment includes a belt configured to permanently house the first therapy electrode and the second therapy electrode. The belt can be further configured to releasably receive the receptacle proximate to at least one of the first therapy electrode and the second therapy electrode. The receptacle can house the conductive fluid, and the belt can electrically couple the receptacle with the wearable therapeutic device.

In one embodiment, method 2000 includes an act of providing instructions (ACT 2010). For example, providing instructions (ACT 2010) can include providing instructions to operate the wearable therapeutic device. In one embodiment, the instructions include at least one instruction directing the subject to dispose the receptacle proximate to at least one of the first therapy electrode and the second therapy electrode (ACT 2015). In one embodiment, the instructions include at least one instruction directing the subject to interface with a user interface to prevent the delivery of an electric shock to the subject (ACT 2020).

The foregoing is illustrative and not limiting, having been presented by way of example. In particular, although many of the examples presented herein involve specific combinations of method acts or system elements, it is understood that those acts and those elements may be combined in other ways. Acts, elements and features discussed only in connection with one embodiment are not excluded from a similar role in other embodiments.

Note that in FIGS. 1 through 20, the enumerated items are shown as individual elements. In actual implementations of the systems and methods described herein, however, they may be inseparable components of other electronic devices such as a digital computer. Thus, actions described above may be implemented at least in part in software that may be embodied in an article of manufacture that includes a program storage medium. The program storage medium includes data signals embodied in one or more of a carrier wave, a computer disk (magnetic, or optical (e.g., CD or DVD, or both)), non-volatile memory, tape, a system memory, and a computer hard drive. The program storage medium can include at least non-transient mediums, and the signals can include at least non-transient signals.

From the foregoing, it is appreciated that the wearable therapeutic device provided herein affords a simple and effective way to automatically apply and immediately provide lifesaving care to a subject during a cardiac event without any human intervention.

Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements to single or plural configurations.

Any embodiment disclosed herein may be combined with any other embodiment, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. Such terms as used herein are not necessarily all referring to the same embodiment. Any embodiment may be combined with any other embodiment in any manner consistent with the aspects and embodiments disclosed herein.

References to "or" should be construed as inclusive so that any terms described using "or" may indicate any of a single, more than one, and all of the described terms. Intervening embodiments, acts, or elements are not essential unless recited as such.

Where technical features in the drawings, detailed description or any claim are followed by references signs, the reference signs have been included for the sole purpose of increasing the intelligibility of the drawings, detailed description, and claims. Accordingly, neither the reference signs nor their absence have any limiting effect on the scope of any claim elements.

One skilled in the art will realize the systems and methods described herein may be embodied in various forms. The foregoing embodiments are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A wearable monitoring and therapeutic device comprising:

at least one defibrillator component comprising a power source;

at least two sensing electrodes, each sensing electrode comprising a metallic surface permanently disposed in a garment;

at least two therapy electrodes, each therapy electrode having a conductive surface, wherein each of the at least two therapy electrodes comprises a replaceable receptacle, each replaceable receptacle comprising at least one dose of conductive fluid, and wherein each replaceable receptacle is configured to release the conductive fluid from the replaceable receptacle and is further configured to be replaced after use, the release of the conductive fluid from the replaceable receptacle configured to decrease impedance between the respective therapy electrode for the replaceable receptacle and skin of a subject, the garment, wherein the garment is configured to be worn about a torso of the subject, the garment comprising a fabric that is stretchable and that is at least one of breathable or moisture wicking, conductive wiring configured to electrically connect the at least two sensing electrodes to the at least one defibrillator component, and at least two pockets, each configured to house a therapy electrode, wherein each pocket comprises a pocket surface configured to be situated between the therapy electrode and the skin of the subject when the therapy electrode is housed in the pocket, and wherein the pocket surface comprises a mesh comprising a conductive metal to lower impedance between the skin of the subject and the conductive surface of the therapy electrode housed in the pocket, wherein the at least two pockets are situated in the garment such that, when the at least two therapy electrodes are inserted into the at least two pockets, at least a first therapy electrode is situated against a front of the subject and at least a second therapy electrode is situated against a rear of the subject; and wherein the at least two sensing electrodes electrically connected to the at least one defibrillator component via the conductive wiring are configured to monitor an ECG of the subject, wherein the at least two therapy electrodes are configured to be electrically connected to the at least one defibrillator component and configured to provide an electric shock to the subject, and wherein the garment is configured to house the at least two sensing electrodes and the at least two therapy electrodes electrically connected to the at least one defibrillator component such that, when the wearable monitoring and therapeutic device is positioned on the subject, the wearable monitoring and therapeutic device accommodates the subject's chest size.

2. The wearable monitoring and therapeutic device of claim 1, wherein the fabric is moisture wicking.

3. The wearable monitoring and therapeutic device of claim 2, wherein the fabric comprises a spandex nylon.

4. The wearable monitoring and therapeutic device of claim 3, wherein the fabric of the garment is configured such that, when the wearable monitoring and therapeutic device is positioned on the subject, the garment exerts between 0.050 and 1.70 lbs. of force on the subject.

5. The wearable monitoring and therapeutic device of claim 3, wherein the conductive metal of the pocket surface comprises silver.

6. The wearable monitoring and therapeutic device of claim 1, wherein the conductive wiring of the garment is configured to stretch to accommodate the subject's chest size.

7. The wearable monitoring and therapeutic device of claim 6, wherein the conductive wiring of the garment is configured in a zigzag pattern.

8. The wearable monitoring and therapeutic device of claim 1, wherein the at least two therapy electrodes comprise three therapy electrodes;

wherein the at least two pockets comprise three pockets; and wherein the three pockets are situated in the garment such that, when the three therapy electrodes are inserted into the three pockets, the first therapy electrode is situated against the front of the subject, the second therapy electrode is situated against the rear of the subject, and a third therapy electrode is situated against the rear of the subject.

9. The wearable monitoring and therapeutic device of claim 1, further comprising an alarm module operatively coupled to the at least one defibrillator component and configured to alert the subject of an impending electric shock to be delivered by the at least two therapy electrodes;

wherein the alarm module comprises one or more response buttons configured to be depressed by the subject to indicate that the subject is conscious in response to the alert to the subject of the impending electric shock; and wherein the alarm module is configured to be disposed on a shoulder strap of the garment.

10. The wearable monitoring and therapeutic device of claim 9, wherein the alarm module comprises a user interface.

11. The wearable monitoring and therapeutic device of claim 10, wherein the user interface of the alarm module comprises the one or more response buttons.

12. The wearable monitoring and therapeutic device of claim 11, wherein the one or more response buttons comprises one response button.

13. The wearable monitoring and therapeutic device of claim 11, wherein the alarm module is configured to alert the subject of the impending electric shock via an audio warning.

14. The wearable monitoring and therapeutic device of claim 11, wherein the alarm module is further configured to alert the subject of the impending electric shock via a haptic warning.

15. The wearable monitoring and therapeutic device of claim 9, wherein the garment is configured to be washable.

* * * * *